US 11,389,170 B2

(12) United States Patent
Mirigian et al.

(10) Patent No.: US 11,389,170 B2
(45) Date of Patent: Jul. 19, 2022

(54) OCCLUSIVE IMPLANTS WITH FIBER-BASED RELEASE STRUCTURES

(71) Applicant: ENDOSHAPE, INC., Boulder, CO (US)

(72) Inventors: Greg Mirigian, Dublin, CA (US); Brad Homann, Brighton, CO (US); Richard Briganti, Bala Cynwyd, PA (US); Troy Chapman, Centennial, CO (US); Dean Carpenter, Boulder, CO (US); Steven Choi, Lafayette, CO (US); Jessi Watson, Steamboat Springs, CO (US); Charles Barkenbus, Longmont, CO (US); Daniel Ashurst, Castle Pines, CO (US); David Willenbrink, Denver, CO (US)

(73) Assignee: ENDOSHAPE, INC., Boulder, CO (US)

( * ) Notice: Subject to any disclaimer, the term of this patent is extended or adjusted under 35 U.S.C. 154(b) by 111 days.

(21) Appl. No.: 16/289,163

(22) Filed: Feb. 28, 2019

(65) Prior Publication Data

US 2019/0314033 A1    Oct. 17, 2019

Related U.S. Application Data

(63) Continuation of application No. PCT/US2017/051859, filed on Sep. 15, 2017.
(Continued)

(51) Int. Cl.
*A61B 17/12* (2006.01)
*A61M 25/09* (2006.01)

(52) U.S. Cl.
CPC .... *A61B 17/12113* (2013.01); *A61B 17/1215* (2013.01); *A61B 17/12031* (2013.01);
(Continued)

(58) Field of Classification Search
CPC .......... A61B 17/12113; A61B 17/1214; A61B 17/12145; A61B 17/1215; A61B 17/12154; A61B 2017/12054; A61B 2017/12063; A61B 2017/12068; A61B 2017/12072; A61B 17/12031; A61B 17/12109; A61B 17/12022–12195
See application file for complete search history.

(56) References Cited

U.S. PATENT DOCUMENTS

| 4,739,768 A | 4/1988 | Engelson |
| 4,813,934 A | 3/1989 | Engelson et al. |

(Continued)

FOREIGN PATENT DOCUMENTS

| CN | 101310681 A | 11/2008 |
| CN | 201380016522.4 | 7/2015 |

(Continued)

OTHER PUBLICATIONS

Boston Scientific Interlock ™ Brochure, 2006.

*Primary Examiner* — Katherine H Schwiker
(74) *Attorney, Agent, or Firm* — Bochner IP, PLLC; Andrew D. Bochner

(57) ABSTRACT

Occlusive implants are provided with various embodiments of active and/or passive release structures. Systems for delivering the occlusive implants as well as methods for making and delivering the implants are also provided.

13 Claims, 17 Drawing Sheets

Related U.S. Application Data

(60) Provisional application No. 62/396,021, filed on Sep. 16, 2016.

(52) U.S. Cl.
CPC .. *A61B 17/12145* (2013.01); *A61B 17/12154* (2013.01); *A61B 2017/12054* (2013.01); *A61F 2230/0091* (2013.01); *A61M 25/0905* (2013.01)

(56) References Cited

U.S. PATENT DOCUMENTS

| | | | |
|---|---|---|---|
| 4,884,579 | A | 12/1989 | Engelson |
| 4,994,069 | A | 2/1991 | Ritchart et al. |
| 5,108,407 | A | 4/1992 | Geremia et al. |
| 5,109,867 | A | 5/1992 | Twyford, Jr. |
| 5,122,136 | A | 6/1992 | Guglielmi et al. |
| 5,250,071 | A | 10/1993 | Palermo |
| 5,261,916 | A | 11/1993 | Engelson |
| 5,304,195 | A | 4/1994 | Twyford, Jr. et al. |
| 5,382,259 | A * | 1/1995 | Phelps ............. A61B 17/12145 606/151 |
| 5,578,045 | A | 11/1996 | Das |
| 5,601,600 | A | 2/1997 | Webster |
| 5,800,455 | A | 9/1998 | Palermo et al. |
| 5,853,422 | A | 12/1998 | Huebsch et al. |
| 5,891,130 | A | 4/1999 | Palermo et al. |
| 5,895,391 | A | 4/1999 | Farnholtz |
| 5,916,235 | A | 6/1999 | Guglielmi |
| 6,027,519 | A | 2/2000 | Stanford |
| RE37,117 | E | 3/2001 | Palermo |
| 6,375,668 | B1 | 4/2002 | Gifford et al. |
| 7,691,124 | B2 | 4/2010 | Balgobin |
| 7,785,361 | B2 | 8/2010 | Nikolchev et al. |
| 8,034,094 | B2 | 10/2011 | Aoba et al. |
| 8,992,545 | B2 | 3/2015 | Cahill |
| 9,339,275 | B2 | 5/2016 | Trommeter et al. |
| 9,375,333 | B1 * | 6/2016 | Aboytes ............. A61B 17/12109 |
| 2001/0002438 | A1 | 5/2001 | Sepetka et al. |
| 2002/0143349 | A1 | 10/2002 | Gifford et al. |
| 2004/0034363 | A1 | 2/2004 | Wilson et al. |
| 2004/0193178 | A1 | 9/2004 | Nikolchev |
| 2004/0220610 | A1 | 11/2004 | Kreidler et al. |
| 2005/0038470 | A1 | 2/2005 | van der Burg et al. |
| 2005/0177182 | A1 | 8/2005 | van der Burg et al. |
| 2005/0192620 | A1 | 9/2005 | Cully et al. |
| 2005/0228438 | A1 | 10/2005 | Sachar et al. |
| 2005/0273135 | A1 | 12/2005 | Chanduszko et al. |
| 2005/0288786 | A1 | 12/2005 | Chanduszko |
| 2006/0116714 | A1 * | 6/2006 | Sepetka ............. A61B 17/12022 606/200 |
| 2006/0122647 | A1 | 6/2006 | Callaghan et al. |
| 2006/0136037 | A1 | 6/2006 | DeBeer et al. |
| 2006/0155323 | A1 | 7/2006 | Porter et al. |
| 2006/0271097 | A1 | 11/2006 | Ramzipoor et al. |
| 2006/0276827 | A1 | 12/2006 | Mitelberg et al. |
| 2007/0010849 | A1 | 1/2007 | Balgobin et al. |
| 2007/0010850 | A1 | 1/2007 | Balgobin et al. |
| 2007/0055302 | A1 | 3/2007 | Henry et al. |
| 2007/0083226 | A1 | 4/2007 | Buiser et al. |
| 2007/0167981 | A1 | 7/2007 | Opolski et al. |
| 2007/0221230 | A1 | 9/2007 | Thompson et al. |
| 2007/0248640 | A1 * | 10/2007 | Karabey ............. A61B 17/12172 424/423 |
| 2007/0276415 | A1 | 11/2007 | Kladakis et al. |
| 2007/0282373 | A1 | 12/2007 | Ashby et al. |
| 2008/0039922 | A1 | 2/2008 | Miles et al. |
| 2008/0119887 | A1 | 5/2008 | Que et al. |
| 2008/0300616 | A1 | 12/2008 | Que et al. |
| 2008/0306503 | A1 | 12/2008 | Que et al. |
| 2009/0025820 | A1 | 1/2009 | Adams |
| 2009/0036877 | A1 | 2/2009 | Nardone et al. |
| 2009/0138023 | A1 | 5/2009 | Johnson et al. |
| 2009/0270974 | A1 | 10/2009 | Berez et al. |
| 2009/0287291 | A1 | 11/2009 | Becking et al. |
| 2009/0312748 | A1 | 12/2009 | Johnson et al. |
| 2010/0070050 | A1 | 3/2010 | Mathis et al. |
| 2010/0160944 | A1 | 6/2010 | Teoh et al. |
| 2010/0168834 | A1 | 7/2010 | Ryan et al. |
| 2010/0174269 | A1 | 7/2010 | Tompkins et al. |
| 2010/0185233 | A1 | 7/2010 | Thommen |
| 2010/0262177 | A1 | 10/2010 | Frigstad et al. |
| 2010/0324586 | A1 | 12/2010 | Miles et al. |
| 2011/0092997 | A1 | 4/2011 | Kang |
| 2011/0184456 | A1 | 7/2011 | Grandfield et al. |
| 2012/0172927 | A1 | 7/2012 | Campbell et al. |
| 2013/0225778 | A1 | 8/2013 | Goodrich et al. |
| 2015/0374884 | A1 | 12/2015 | Goodrich |
| 2016/0024239 | A1 | 1/2016 | Goodrich et al. |

FOREIGN PATENT DOCUMENTS

| | | |
|---|---|---|
| EP | 13740740.9 | 2/2016 |
| EP | 13740740.9 | 12/2017 |
| JP | 2014-554889 | 10/2016 |
| WO | WO 1994/06503 A1 | 3/1994 |
| WO | WO PCT/US2013/023306 | 3/2013 |
| WO | WO PCT/US2017/051859 | 2/2018 |

* cited by examiner

OCCLUSIVE IMPLANTS WITH FIBER-BASED RELEASE STRUCTURES

CROSS-REFERENCE TO RELATED APPLICATIONS

This application is a continuation of PCT Patent Application No. PCT/US17/51859, filed Sep. 15, 2017, which claims priority to U.S. Provisional Application No. 62/396,021, filed Sep. 16, 2016, both of which applications are incorporated by reference herein in their entireties for all purposes.

FIELD

The subject matter described herein relates to occlusive medical devices implantable in the human body for purposes of treating vascular defects, occluding vascular structures to inhibit blood flow, or treating other diseases or conditions, where the occlusive devices include fiber-based components that assist in delivery and release of the occlusive implant from a delivery system.

BACKGROUND

During many clinical procedures, a physician requires the reduction or complete stoppage of blood flow to a target region of the patient's body to achieve therapeutic benefit. Occlusive implants are often used for this purpose. Occlusive implants can be used to inhibit blood flow for a wide variety of applications, two examples of which are the occlusion of blood vessels and the occlusion of aneurysms.

Physicians can be motivated to use occlusive implants for vessel occlusion in order to treat a number of situations, for example, arteriovenous malformations (AVMs), traumatic fistulae, some aneurysm repair, uterine fibroid and tumor embolization. For these clinical treatments, the blood flow through a target section of a blood vessel must be occluded (i.e., significantly reduced or stopped altogether). The delivered implant induces an initial reduction of blood flow through a simple mechanical blockage which in turn triggers the body's natural clotting process to form a more complete blockage comprised of the thrombus adhered to the implant.

An aneurysm often takes the form of a relatively localized, blood-filled bulge in a weakened wall of a blood vessel. Aneurysms can occur in any arterial blood vessel, with examples including cerebral aneurysms, aortic aneurysms affecting the thoracic aorta, and abdominal aortic aneurysms. As an aneurysm increases in size, the risk of rupture increases. A ruptured aneurysm can lead to bleeding and subsequent hypovolemic shock, which in turn can lead to death. For example, cerebral aneurysms, also known as intracranial or brain aneurysms, occur commonly in the anterior cerebral artery, which is part of the circle of Willis, and in the internal carotid artery. Rupture of a cerebral aneurysm can cause severe hemorrhagic stroke. Aneurysms can also be a nidus for clot or thrombus formation. A thrombus released from a cerebral aneurysm can cause severe ischemic stroke.

Physicians can be motivated to treat aneurysms by the implantation of one or more occlusive implants within or over the aneurysm. The occlusive implant can cause a thrombus to form and remain within the confines of the aneurysm, which in turn can decrease the risk of rupture and promote the healing response. In many cases, aneurysms treated in such a manner are almost entirely healed within a manner of months or weeks.

Occlusive implants are typically delivered to the vessel or aneurysm with a sterile catheter percutaneously inserted into the body and routed through the subject's vasculature to the target site. The occlusive implant is pushed out of an open distal end of the catheter, using a slidable pusher within the catheter, into the aneurysm or vessel. Once deployed in the body the implant can mechanically inhibit blood flow and promote thrombus formation on or around the implant until the vessel or aneurysm is fully occluded.

During the delivery process it is often desirable to maintain control of the position of the implant with respect to the open distal end of the catheter and control the timing of release of the distal end and/or the proximal end of the implant from the pusher and/or catheter-based delivery system. While many types release mechanisms are known in the art, these release mechanisms can suffer from numerous drawbacks, including undue complexity, difficulty to manufacture, lack of reliability, stiffness, and resistance to advancement through the catheter, to name a few. As such, needs exist for improved release mechanisms.

SUMMARY

Provided herein are a number of example embodiments of occlusive implants and delivery systems having one or more fiber-based release structure components, as well as example embodiments of methods of their use and manufacture. In many embodiments, the fiber-based release structures are formed from the same fibers that are used to form a braid covering of the implant. The braid can provide benefits such as increasing the tensile strength of both the implant the release structure. The braid can also provide a lubricious surface for the occlusive implant. The presence of one or more release structures provides control to the medical professional (e.g., a physician) during delivery, allowing the implant to be advanced and retracted multiple times. A distal release structure can allow manipulation of the position of the distal end of the implant with respect to the proximal end, which can be beneficial in lengthening or foreshortening the implant, and also in creating a coil pack.

In some embodiments, the fiber-based release structures are part of an active release system, where additional action beyond advancement of the implant from within the catheter alone is needed to release the implant. In other embodiments, the fiber-based release structures are part of a passive release system, where the implant remains connected to the delivery system while within the catheter, and is released generally upon exiting the catheter's open distal end.

Also provided herein are a number of example embodiments of occlusive implants and delivery systems having passive release structures that may or may not be fiber-based, or may be only partially fiber-based, as well as example embodiments of methods of their use and manufacture. Certain example embodiments of the passive release structures utilize rigid or substantially rigid interlocking components having male and corresponding female configurations. These passive release structures can be used as part of a system having active release components elsewhere (e.g., active distal release in combination with passive proximal release).

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The present subject matter is described in the context of the use of an occlusive implant that can take the form of a coil, which is implanted within an aneurysm or blood vessel to obstruct blood flow within or to that aneurysm or blood vessel. The present subject matter is not limited only to implants that can take the form of a coil, as the subject matter is similarly applicable to implants that have either multiple coils or structures or forms other than those of a coil. Likewise, the present subject matter is not limited only to the occlusion of aneurysms or blood vessels (e.g., peripheral vessel occlusion) as the subject matter is applicable to the treatment of many types of disease where passive or active release of an implant is desirable, including but not limited to the treatment of septal defects in the heart, the treatment of left atrial appendages, and the like.

Example Embodiments of Systems with Fiber Loop Release Structures

Figure 1A:
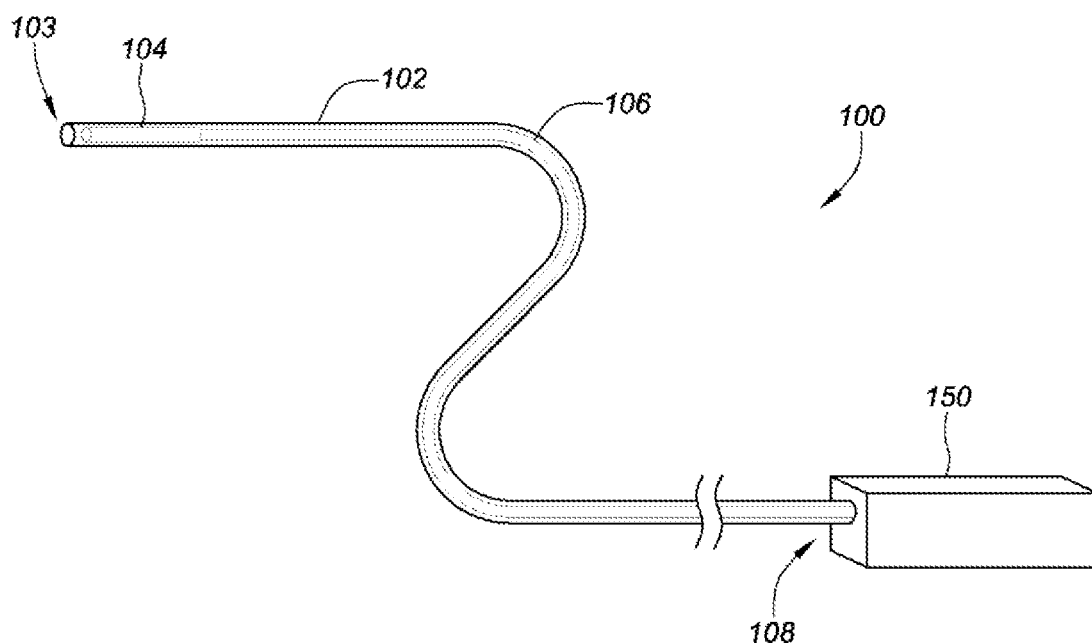
FIG. 1A is a perspective view depicting an example embodiment of a delivery system.

FIG. 1A is a perspective view of an example embodiment of implant delivery system 100, which can be used with all embodiments described herein. System 100 includes an elongate tubular member 102, which can be configured as a catheter, a micro-catheter, a sheath, or a trocar. Tubular member 102, which for ease of discussion will be referred to as catheter 102, can be percutaneously introduced into a patient's vasculature and then advanced to a target treatment site, either directly or with the aid of a guidewire. In some embodiments, tubular member 102 can slide within a larger tubular member, such as a guide catheter (not shown).

Catheter 102 includes an open distal end 103 from which an occlusive implant 104 can be delivered. Occlusive implant 104 is slidable within catheter 102 and can be advanced with an elongate pusher member (referred to herein for brevity as a pusher) 106 that is also slidable within catheter 102. A proximal end 108 of catheter 102 is coupled with a proximal control device 150 that resides outside of the patient and comprises one or more controllable inputs (not shown) for use by the medical professional to control the delivery (implantation) procedure. For example, proximal control device 150 can have one or more lock mechanisms that can lock the various slidable components so that they do not move with respect to each other. Proximal control device 150 can also have one or more ports for introducing components of system 100 and flushing.

Figure 1B:
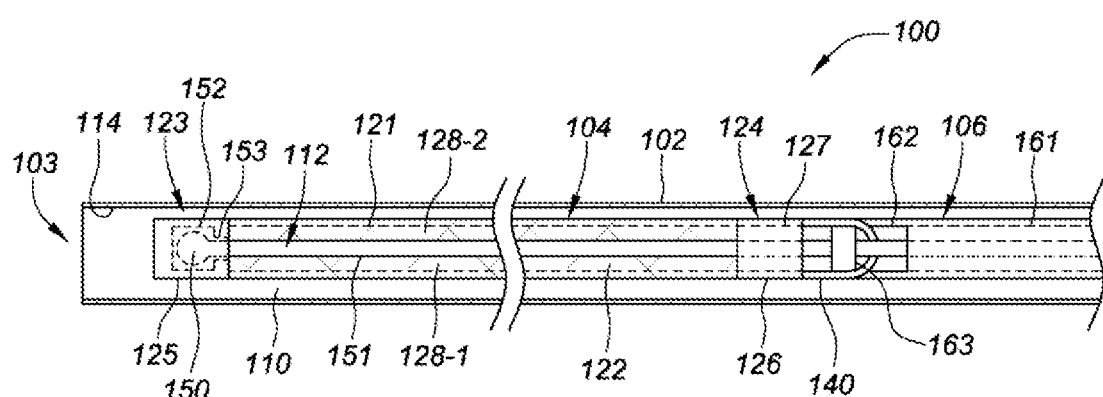
FIG. 1B is a partial cross-sectional view depicting another example embodiment of a delivery system having a fiber loop release structure.

FIG. 1B is a partial cross-sectional side view of an example embodiment of system 100. Catheter 102 is shown with implant 104 and pusher 106 within the catheter's inner lumen 110. Implant 104 is depicted here in a generally straight or elongate shape (e.g., a non-coiled shape), but can be configured, in some embodiments, to deform into a secondary and even a tertiary shape once it exits open distal end 103 (see, for example, implant 104 with a secondary helical coil shape as shown in FIG. 2B). Implant 104 can include an elongate body 121 (shown as obscured with a dashed line) that is covered or wrapped with a braid 122. Implant 104 also includes a distal end or end region 123 and a proximal end or end region 124. In this embodiment, a distal hub 125 is in distal end region 123 and a proximal hub 126 is in proximal end region 124. Hubs 125 and 126 can be tubular members such as radiopaque marker bands or polymeric sleeves.

Body 121 can have a strand-like or wire-like structure. Body 121 can be cylindrical or substantially cylindrical and can have a length that greatly exceeds its diameter or width. Several examples of body 121 are depicted in FIGS. 3A-1, 3A-2, 3A-3, 3B-1, 3B-2, 3B-3, 4A-1, and 4A-2 of U.S. Publ. No. 2015/0257765, which is incorporated by reference herein in its entirety and for all purposes. Body 121 can be formed from any desired biocompatible material, preferably with shape retention capability (if that shape retention trait is desired). Prior to introduction into the patient, body 121 can be instilled with the secondary and/or tertiary shape, such as by heat setting. Examples of suitable biocompatible materials with shape retention capabilities include polymers (such as radiopaque polymers and radiopaque composite polymers), platinum, platinum alloys, nitinol, stainless steel, and the like. Examples of suitable radiopaque polymers are described in U.S. Publ. No. 2013/0225778, U.S. Publ. No. 2015/0374884, and U.S. Publ. No. 2016/0024239, all of which are incorporated by reference herein in their entireties for all purposes.

In many embodiments, body 121 is covered or wrapped in braid 122 such that braid 122 conforms to the shape of body 121. For example, if body 121 is cylindrical or substantially cylindrical with a given diameter, then braid 121 can also be cylindrical or substantially cylindrical with a matching diameter. Braid 122 can be applied with the assistance of a conventional braiding machine. The braid 122 can be of any desired variety, e.g., 4 line, 6 line, and so forth.

Braid 122 can be composed of numerous strands of filaments or fibers. Braid 122 can be formed by braiding (e.g., crossing) one individual fiber with one or more other individual fibers. However, as shown in FIG. 1B, many fibers are grouped together, and those fiber groupings are then woven together to form braid 122. Two such fiber groupings are shown with reference numerals 128-1 and 128-2. When braided, each fiber grouping as a whole has a tendency to flatten out over body 121, such that the width of the fiber grouping is greater than the height of the fiber grouping from the exterior surface of body 121.

In the embodiment of FIG. 1B, the entirety of body 121 (while in the generally elongate or straight shape) between hubs 125 and 126 is surrounded and in contact with braid 122 (e.g., such that body 121 is not exposed to the exterior in gaps between the braid weavings), although in other embodiments only a portion of body 121 is covered, such that a length of body 121 can be left exposed or body 121 can be exposed in gaps between the braid weavings. Although gaps in braid 122 can be present, braid 122 preferably travels over the entire circumferential periphery of body 121, remaining in contact with body 121. Such would not be the case if body 121 were in a helical coil shape, and then braid covered only the outer diameter of the helical coil (although such a configuration is within the scope of this disclosure).

The ends of braid 122 can be anchored in place with distal hub 125 and proximal hub 126 such as with the assistance of crimping, adhesive, or both. The length of braid 122 between hubs 125 and 126 can also be anchored in place with adhesive or other means, if desired. In some embodiments, the braid 122 is closely wound over and in direct contact with the outer surface of body 121 such that no additional attachment is necessary. In many embodiments, braid 122 is adapted to remain in place on body 121 without movement on the surface of body 121 (or without significant movement that would lead to bunching of the braid) while body 121 is advanced through the inner lumen of catheter 102. Also, in many embodiments implant 104 deforms into the secondary and/or tertiary shapes while braid 122 remains in place on body 121 without movement on the surface of body 121.

The use of braid 122 can be advantageous in that it reduces surface friction between body 121 and the interior surface 114 of catheter 102. When configured for use as an implantable coil, implant 104 can have a significant length within inner lumen 110, even greater than unbraided implantable coils made from traditional materials like platinum. For example, depending on the vessel size, implants 104 can be selected from those having a length from several centimeters (cm) to 100 cm or greater. The tight constraints of the anatomy impose even tighter constraints on the diameter of inner lumen 110. For example, a typical 3 French catheter 102 can have an inner diameter of 0.027 inches, while a 4-5 French catheter can have an inner diameter of 0.038 inches. These small diameters, coupled with the significant length of implant 104, can result in large surface area of implant 104 that contacts the inner surface of catheter 102 resulting in a high surface friction between implant 104 and catheter 102. This is especially true when catheter 102 is polymeric and body 121 is formed from a radiopaque polymer. Surface friction can also increase when the catheter is negotiating tortuous bends that are often encountered in the anatomy. A surface friction that is too high makes it difficult, or even impossible, for the medical professional to advance the implant from within catheter 102, and thus imposes a limitation as to the maximum length of implant that can be used.

The use of braid 122 can lower this surface friction considerably. It has been found that polymeric materials having sufficient flexibility such as ultra-high-molecular-weight polyethylene (UHMWPE), polytetrafluoroethylene (PTFE), fluorinated ethylene propylene (FEP), or other polypropylenes, when used for braid 122 can significantly reduce the surface friction on the implant 104, when moving through catheters formed from polyether block amide (PEBAX), nylons, polyurethanes, or thermoplastic elastomers, with or without fluorinated polymer internal linings. The presence of braid 122 also increases the tensile strength of the overall implant itself, making the implant less subject to stretching and tensile strain-induced rupture. UHMWPE, for example, can also significantly increase the tensile strength of the implant.

Referring back to FIG. 1B, a control wire 112 (sometimes referred to as a distal wire or core wire) is used to control the release of the distal end 123 and proximal end 125 of implant 104. Many different release structures can be used to accomplish release of the distal end of implant 104, including any and all of those set forth in U.S. Publ. No. 2014/0039542, which is incorporated by reference herein in its entirety for all purposes.

In this example embodiment, control wire 112 has an enlarged distal end 150 (e.g., in the shape of a ball, block, tab, etc.) with a width that is relatively wider than control wire's shaft 151. Enlarged distal end 150 resides within a chamber or lumen 152 within distal hub 125, which also has a proximal opening 153 with a smaller width than that of enlarged distal end 150. As a result, distal end 150 is maintained within chamber or lumen 152 until such time as the medical professional decides to remove it, typically after implant 104 is suitably positioned within the aneurysm, vessel, or other vascular defect. At that time, a sufficient proximally-directed force is exerted on shaft 151 to cause enlarged distal end 150 to snap through the smaller proximal opening 153 and exit distal hub 125, thereby releasing distal end 123 of implant 104 from control wire 112.

As shown here, control wire 112 is positioned alongside the majority of the length of implant 104 and through a lumen 127 in proximal hub 126. A fiber loop 140 extends proximally from the proximal terminus of proximal hub 126. Fiber loop 140 is releasably held within a recess or window 162 in the tubular pusher 106, which has an inner lumen 161 in which control wire 112 can be slidably housed. Although a gap is shown between the distal pushing surface 163 of pusher 106 and the proximal terminus of proximal hub 126, during advancement of implant 104 these two structures would be in contact.

After release of enlarged distal end 150 from distal hub 125, the proximal withdrawal of control wire 112 is continued until the distal terminus of distal end 150 passes fiber loop 140. At that point, control wire 112 is no longer in position to maintain fiber loop 140 within recess 162 and the proximal end 124 of implant 104 is released from pusher 106, resulting in release of the entirety of implant 104 from pusher 106.

Figure 1C:
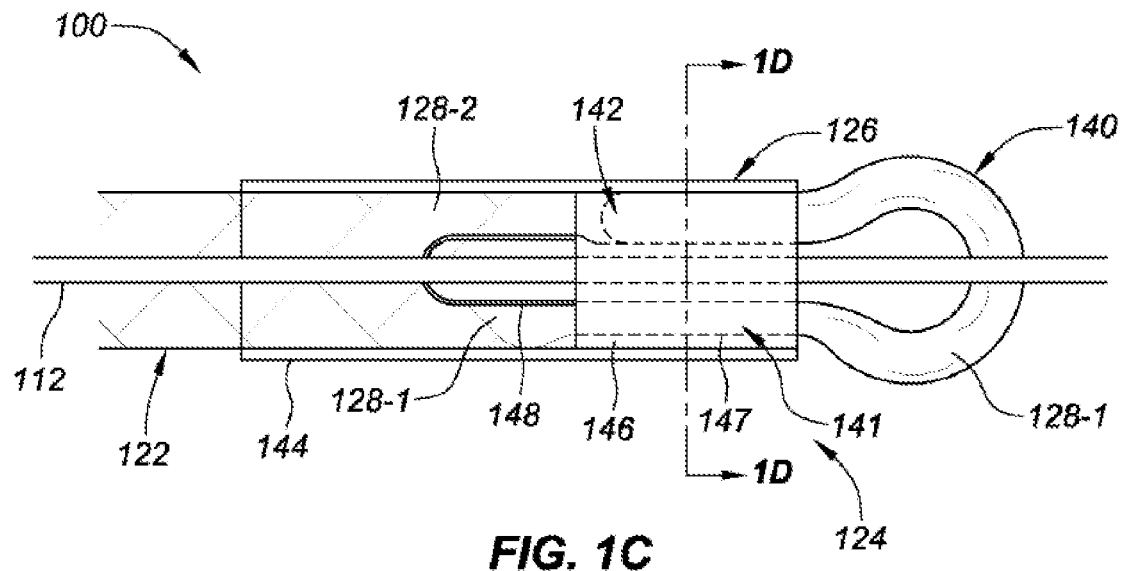
FIG. 1C is a partial cross-sectional view depicting another example embodiment of a delivery system having a fiber loop release structure.

FIG. 1C is a partial cross-sectional view depicting another example embodiment of system 100. Here, proximal hub 126 of proximal end region 124 includes an outer tubular member 144 coupled over an inner tubular member 146. An inner lumen 147 is present within inner tubular member 146 that allows control wire 112 to pass. Access to lumen 147 is through an opening 148, shown here as a skive, in outer tubular member 144. In many embodiments, inner tubular member 146 can be configured as a radiopaque marker band, with outer tubular member 144 formed from a polymeric material such as polyether ether ketone (PEEK), in which opening 148 can be readily formed.

Viewing the arrangement distally to proximally in FIG. 1C, control wire 112 passes alongside braid 122, then outer tube 144, then through opening 148 and into inner lumen 147 of inner tube 146, out of the open proximal terminus of inner lumen 147, and past loop 140. Like in FIG. 1B, braid 122 is again shown with two of the two or more fiber groupings labeled 128-1 and 128-2.

Figure 1D:
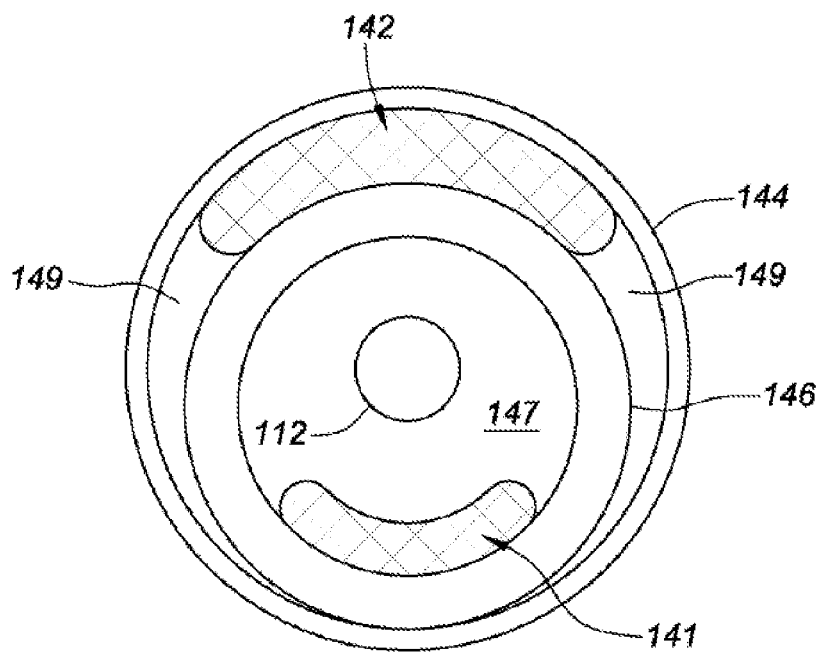
FIG. 1D is a cross-sectional view taken along line 1D-1D of FIG. 1C.

Various manners of formation of loop 140 are now discussed with further reference to FIG. 1D, which is a cross-sectional view taken along line 1D-1D of FIG. 1C. A fiber grouping 128-1 is routed from the braid covering 122 through inner lumen 147 (this section of grouping 128-1 is referred to here with numeral 141). After exiting the proximal terminus of inner lumen 147, grouping 128-1 forms loop 140. Grouping 128-1 then proceeds back into implant 104 within inner lumen 149 of outer tube 144, but not within inner lumen 147 of inner tube 146 (referred to as section 142 in FIGS. 1C and 1D). The terminus of section 142 is shown here as being generally in the same position as the interface between inner tubular member 146 and braid 122, although section 142 can continue further distally, e.g., such that the terminus of section 142 is between braid 122 and outer tubular member 144. Conversely, section 142 need not extend as far distally as shown in FIG. 1C, so long as section 142 is adequately secured within proximal hub 126.

Section 142 can be secured in position within lumen 149 in any desired manner, such as with the use of adhesive or crimping. Similarly, section 141 can be secured in position within lumen 147 in various manners, preferably with the use of adhesive. For example, adhesive can be applied to fiber loop 140 such that it wicks into sections 141 and 142. Adhesive can also be applied into inner lumens 147 and 149, although sufficient open space is desired within inner lumen 147 to allow control wire 112 to slide therethrough.

Although loop 140 is described as being formed with one braid grouping 128-1, loop 140 can be formed from any number of one, two, three, or more braid groupings, including all of the braid groupings constituting braid covering 122. In some embodiments, only a portion of one or more braid groupings is used to form loop 140. In some embodiments, only a single fiber is used to form loop 140. When less than all fibers are used, the excess fibers can be trimmed away. Any combination of the aforementioned variations can be implemented.

Formation of loop 140 using the same one or more fibers as are used in braid 140 provides a loop with significant tensile strength and also avoids the presence of a junction, seam, or other coming-together such as would be the case if a discrete loop were bonded or crimped to the end of implant 104. Thus, fiber loop 140 can be described as integrally or seamlessly connected with braid 122. The presence of a seam or junction between discrete components introduces a susceptibility to breakage and could result in premature release of implant 104. If entirely separated, the broken loop could also result in the formation of an occlusion in some other undesired area in the vasculature. The entire description of loop 140 and its formation herein can be likewise applied to the formation of a loop on the opposite (distal) end of implant 104, e.g., for use in a distal release mechanism (such as one created with control wire passing through a distal loop) or for connecting multiple implants as will be described below.

Figure 1E:
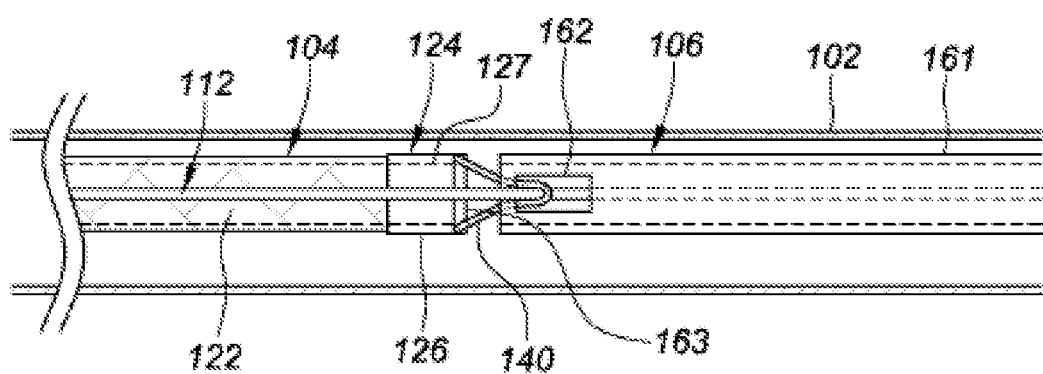
FIG. 1E is a partial cross-sectional view depicting another example embodiment of a delivery system having a fiber loop release structure.

FIG. 1E is a partial cross-sectional view depicting another example embodiment of delivery system 100. This embodiment is similar to that described with respect to FIGS. 1B-1D except that control wire 112 exits lumen 161 of pusher 106 through recess (or window) 162 while loop 140 extends proximally from the implant's proximal end region 124 into lumen 161 of pusher 106 and around control wire 112 in or adjacent to recess 162. The routing of loop 140 is essentially reversed from the routing depicted in FIG. 1B, and control wire 112 continues alongside implant 104 past proximal end region 124 without entering end region 124 as described with respect to FIGS. 1B-1D. Loop 140 can be formed in the same fashion as described with respect to FIGS. 1C-1D. However, because control wire 112 does not pass through end region 124, inner lumen 147 is not required and thus loop 140 can be held within end region 124 in a different fashion. For example, the portion of the fiber grouping that proceeds back into implant 104 (e.g., section 142 in FIGS. 1C and 1D) can be held in place with adhesive (e.g., such as those described herein) or crimping, or with the use of an insert that is adhered or crimped in place. Although not shown, in this embodiment enlarged distal end 150 of control wire 112 can detachably couple with distal hub 125 in a manner similar to that shown and described in FIG. 1B. Other manners of attachment with distal hub 125 can also be used.

Figure 2A:
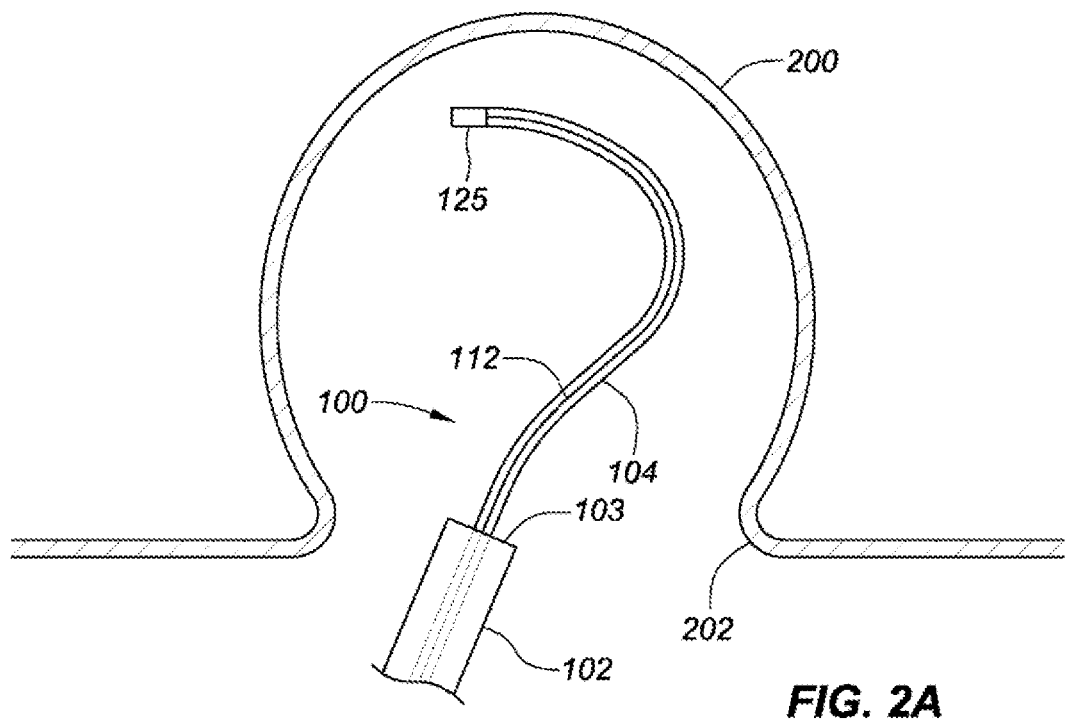
FIGS. 2A-2B are partial cross-sectional views depicting another example embodiment of a delivery system for an occlusive implant at various stages of deployment within an aneurysm.
Figure 2B:
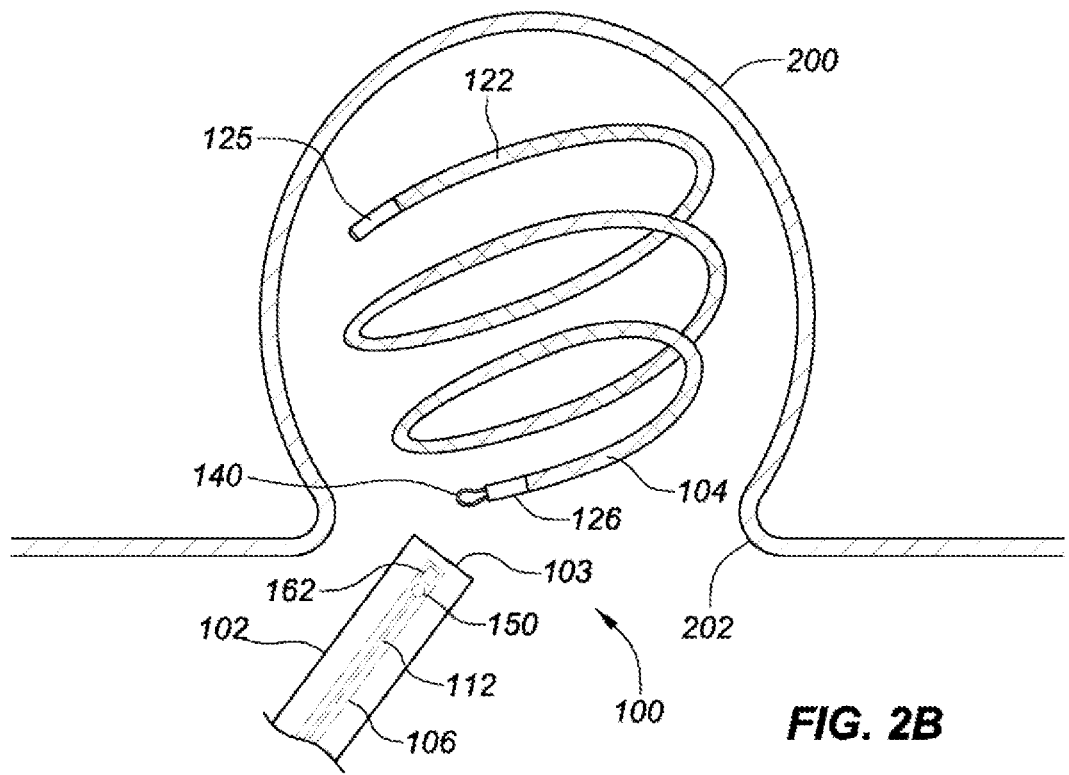

FIGS. 2A and 2B are partial cross-sectional views depicting stages of delivery of implant 104 into an aneurysm 200. In FIG. 2A, distal end 103 of catheter 102 has been positioned in proximity with a target deployment site, such as the neck 202 of aneurysm 200. Pusher 106 (not shown) has been distally advanced to partially deploy implant 104 from distal end 103 and into aneurysm 200. Implant 104 has begun to assume its secondary shape, which in this embodiment is in the form of a helical coil. Control wire 112 is still attached both at the distal hub 125 and proximal hub 126 (not shown). If the medical professional desires to withdrawn implant 104 back into catheter 102, then this can be done simply by withdrawing pusher 106.

In FIG. 2B, pusher 106 has advanced implant 104 entirely from within catheter 102. Control wire 112 has been detached from both distal hub 125 and proximal hub 126. Loop 140 is visible extending proximally from proximal hub 126 of implant 104, which in this embodiment has assumed its full helical shape. Any other desired shape can be formed, such as shapes that coil in one, two, or three-dimensions, ring-like shapes, multi-lobed shapes, or otherwise. At this point, catheter 102 can be withdrawn and implant 104 can remain in place to promote the formation of a thrombus within aneurysm 200 for the purpose of healing. The identical deployment sequence is used for occluding vessels.

Figure 2C:
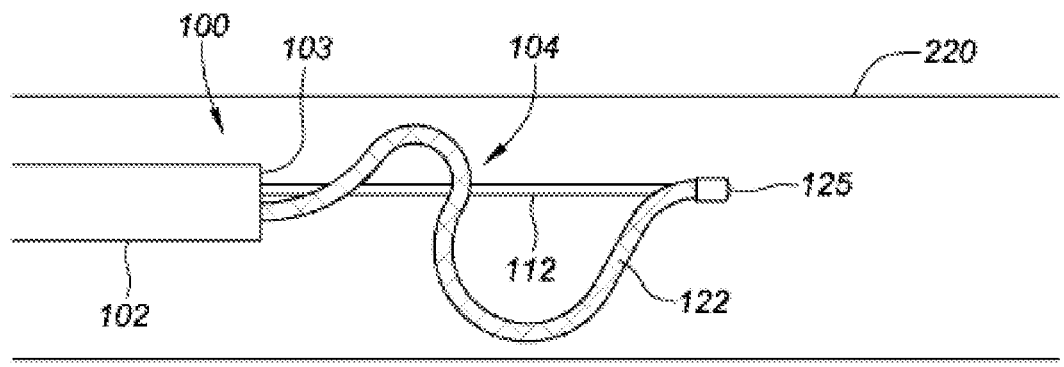
FIGS. 2C-2E are partial cross-sectional views depicting another example embodiment of a delivery system for an occlusive implant at various stages of deployment within a blood vessel.
Figure 2D:
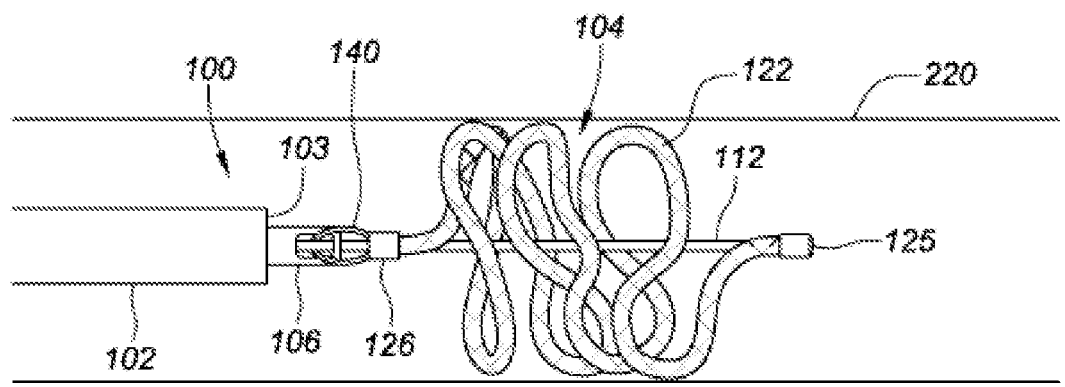
Figure 2E:
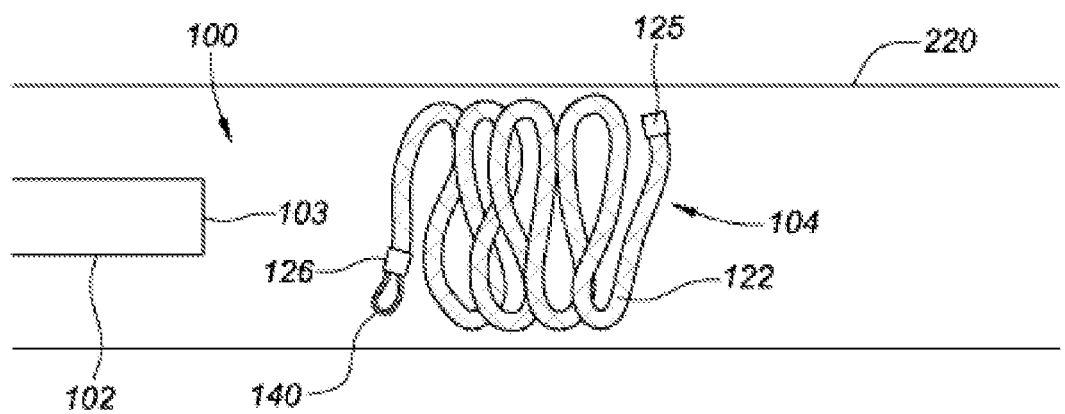

FIGS. 2C-2E are partial cross-sectional views depicting the use of system 100 at various stages of deploying implant 104 for the purpose of occluding a blood vessel 220. In FIG. 2C, distal end 103 of catheter 102 has been advanced into proximity with a target site in vessel 220, and while both implant 104 and control wire 112 have been advanced partially out of catheter 102, a greater length of implant 104 has been advanced while maintaining control wire 112 in a relatively stationary position with respect to catheter 102. This can be achieved by advancing pusher 106 (not shown) distally over control wire 112 while holding control wire 112 in place. The result is that implant 104 begins to coil or bunch within vessel 220 at the target site as shown in FIG. 2C.

FIG. 2D depicts a subsequent stage where implant 104 has been fully advanced from within catheter 102. Pusher member 106 is visible extending from open distal end 103 of catheter 102 after having been advanced as far as desired by the physician while maintaining control wire 112 relatively stationary. As a result, implant 104 has coiled into a tight pack or bunch within vessel 220.

FIG. 2E depicts implant 104 in the deployed packed or bunched state after removal of control wire 112 from distal hub 125 and from proximal fiber loop 140. In this position, implant 104 mechanically blocks blood flow within vessel 220 and will begin to cause the formation of a clot in and around the tight coil pack to further occlude the vessel.

Figure 2F:
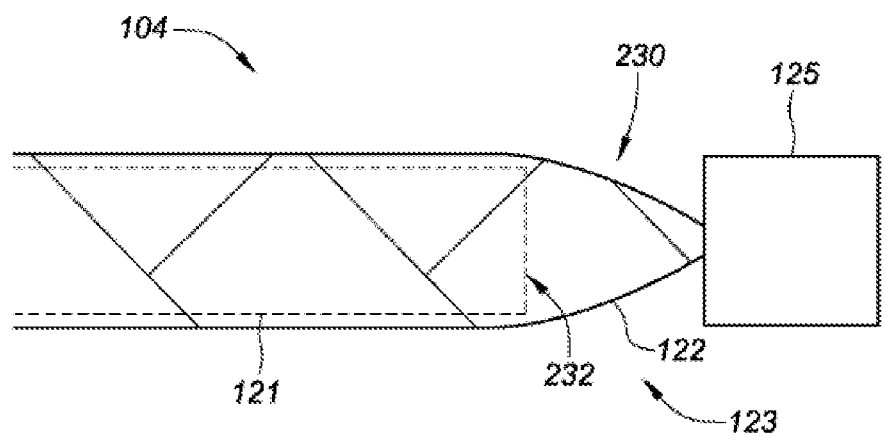
FIG. 2F is a side view depicting another example embodiment of an occlusive implant.

FIG. 2F depicts distal end region 123 of another example embodiment of implant 104. Here, implant 104 includes a hinge 230 between distal hub 125 and distal terminus 232 of body 121 (shown with dashed line indicating position obscured by braid covering 122). In this embodiment, braid covering 122 extends along body 121 and continues past distal terminus 232 and couples with distal hub 125. Braid covering 122 can couple with distal hub 125 in a secure fashion, such as with adhesive (e.g., such as those described herein), soldering, welding, crimping, or other manners of attachment known to those of ordinary skill in the art. The absence of the underlying body 121 in the region of hinge 230 permits braid covering 122 to flex or bend to a greater degree than if body 121 extended into hub 125. Braid covering 122 in the region of hinge 230 thus acts as a living hinge that allows distal hub 125 to more readily (or easily) deflect or rotate with respect to body 121.

Figure 2G:
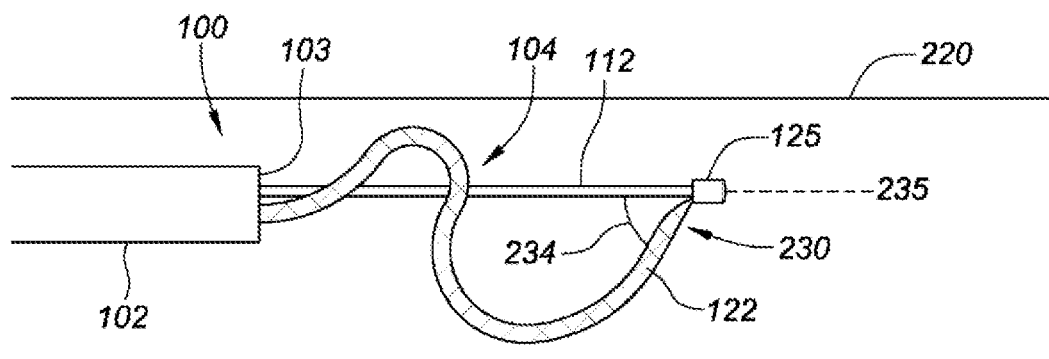
FIGS. 2G-2I are partial cross-sectional views depicting another example embodiment of a delivery system for an occlusive implant at various stages of deployment within a blood vessel.
Figure 2H:
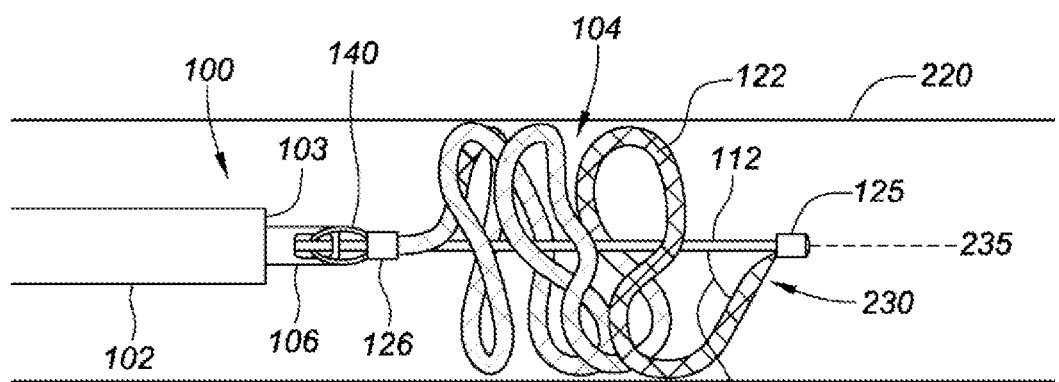
Figure 2I:
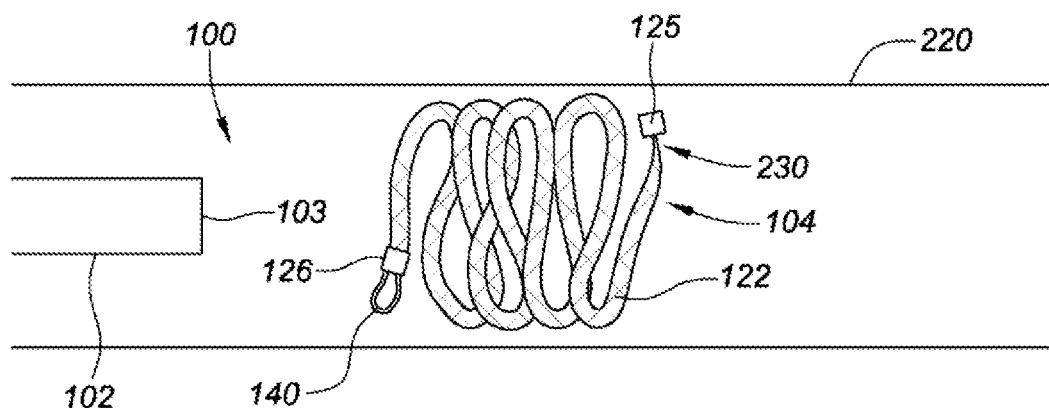

FIGS. 2G-2I are partial cross-sectional views similar to FIGS. 2C-2E but instead depicting this embodiment of implant 104 with hinge 230. As can be seen in FIGS. 2G and 2H, the presence of hinge 230 allows a longitudinal axis of the body of implant 104 to approach distal hub 125 at an angle 234 compared to longitudinal axis 235 of wire 112 (or catheter 102). This reduces stresses in system 100. For example, the stiffness of implant 104 is effectively reduced and hub 125 applies less force to wire 112, which in turn reduces the likelihood that wire 112 will bend to one side. Also, the stress applied to body 121 (not shown) and braid covering 122 of implant 104 is reduced, as implant 104 does not have to bend with as high a degree of curvature as the embodiment of FIGS. 2C and 2D.

While hinge 230 is described as being immediately adjacent distal hub 125, this configuration can also (or alternatively) be placed at proximal hub 126 to provide for a hinge at that location. Thus, implant 104 can have a hinge adjacent distal hub 125 and/or proximal hub 126. If one of hubs 125 and 126 is configured without a hinge, then flexible body 121 can extend into (or otherwise secured directly to) that respective hinge-less hub.

Figure 3:
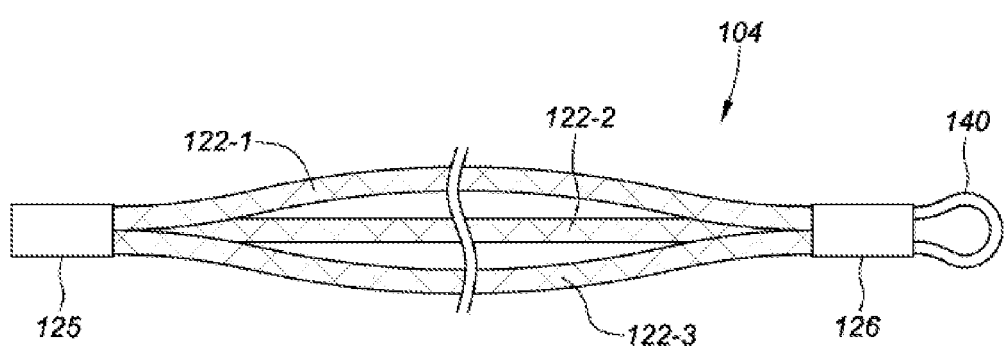
FIG. 3 is a side view depicting an example embodiment of an occlusive implant with multiple coils.

Implant 104 can include one or more strand-like bodies (e.g., coils) connected between distal hub 125 and proximal hub 126. FIG. 3 depicts an example embodiment of implant 104 having three strand-like bodies, each having braid coverings 122-1, 122-2, and 122-3. The multiple bodies can be coupled together with hubs 125 and 126, which can be radiopaque markers, fasteners, crimps, or only bonds formed from adhesive. Each body can be configured to assume the same or a different secondary and/or tertiary shape. For example, each body can form a helical coil, a multi-lobe shape, or otherwise. All of the embodiments of system 100 described herein can utilize an implant 104 having only one strand-like body or more than one strand-like body, unless noted otherwise.

Figure 4A:
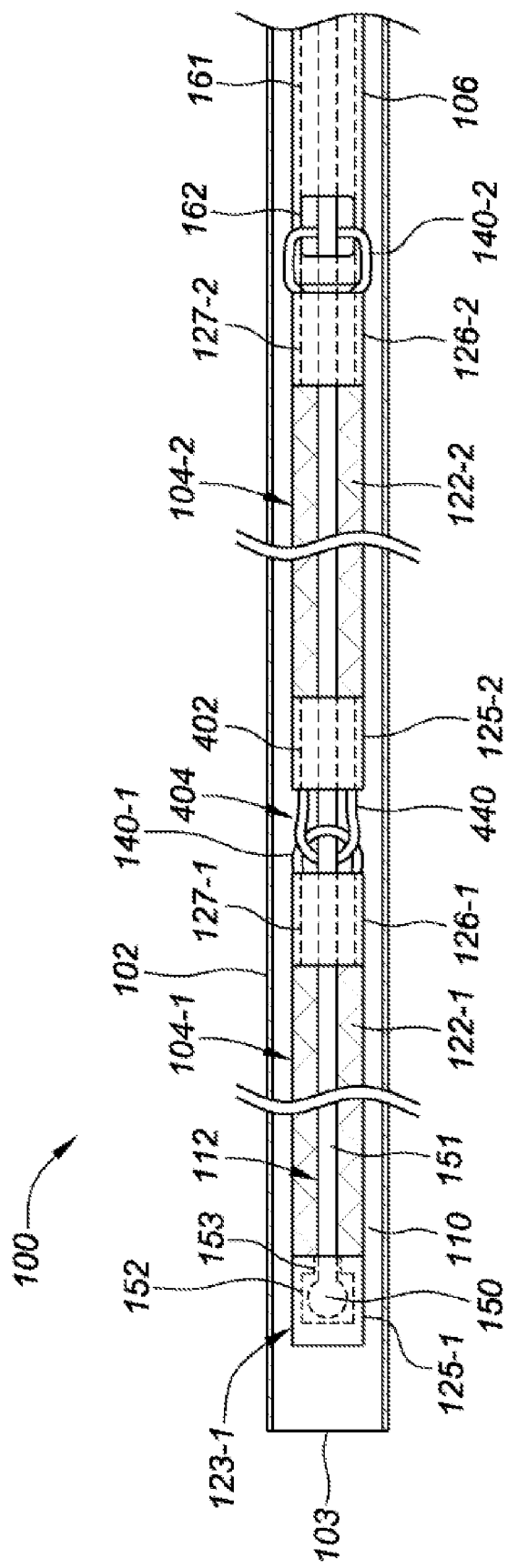
FIG. 4A is a partial cross-sectional view depicting another example embodiment of a delivery system having fiber loop release structures.

FIG. 4A is a partial cross-sectional view depicting an example embodiment of system 100 adapted for delivery of multiple implants 104. As can be seen here, a first, distally-positioned implant 104-1 is releasably coupled to a second, distally-positioned implant 104-2, which is in turn releasably coupled with pusher 106, such that both implants 104-1 and 104-2 are deployable from catheter distal end 103 with pusher 106. Although two coils are shown here, any number of two or more implants 104 can be releasably coupled together and delivered from catheter 102.

As noted earlier, any desired type of controllable distal release structure can be used. Like with FIG. 1B, enlarged distal end 150 of control wire 112 is detachably coupled within chamber 152 of distal hub 125-1 of distal end region 123-1 of the distalmost implant 104-1. Control wire 112 extends proximally along implant 104-1, through lumen 127-1 of distal hub 126-1, through loop interlock 404 (described in more detail with respect to FIG. 4B), through inner lumen 402 of distal hub 125-2, along implant 104-2, through inner lumen 127-2 of proximal hub 126-2, into lumen 161 of pusher 106, past recess 162 and fiber loop 140-2, and continuing the length of catheter 102 to the proximal control device (not shown).

Figure 4B:
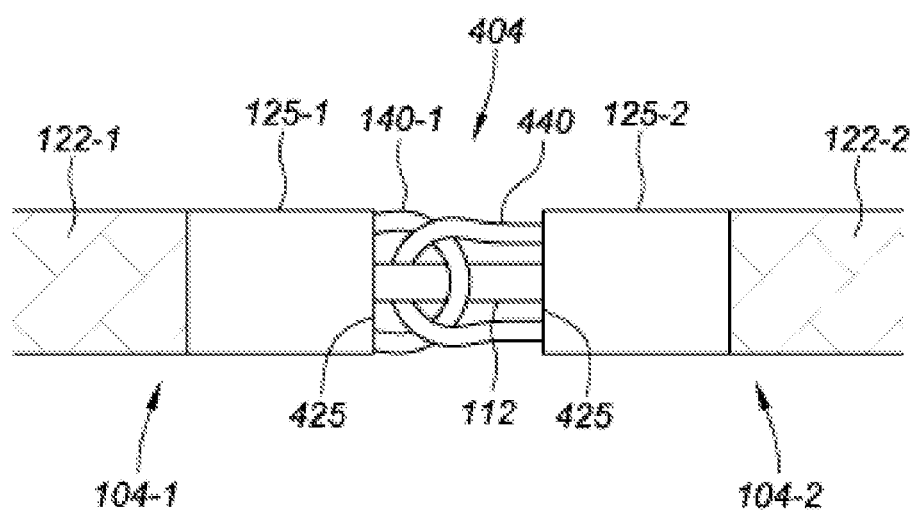
FIG. 4B is an enlarged side view of a fiber interlock structure of the example embodiment of FIG. 4A.

FIG. 4B is a side view of loop interlock 440 between implants 104-1 and 104-2. Depending on the lateral position of implants 104-1 and 104-2 with respect to each other, the apparent position of the loops of interlock 440 with respect to control wire 112 may vary. With the perspective shown here, loop 140-1 of distal implant 104-1 extends proximally from the proximal terminus 426 of proximal hub 126-1 and passes a first side (here, the underside) of loop 440 and then passes a second, opposite side (here, the top side) of control wire 112. Conversely, loop 440 extends distally from distal terminus 425 of distal hub 125-2, over the second side (here, the top side) of loop 140-1 and then passes the first, opposite side (here, the underside) of control wire 112. If the lateral position of the hubs with respect to each other changes, then a first one of the loops may appear to extend around the control wire 112, while the other, second one of the loops appears to extend around only the opposite first loop (extending around control wire 112).

Thus, in this embodiment, each implant can be sequentially released as control wire 112 is drawn further back. For example, the distal most implant 104-1 can be released by withdrawing enlarged end 150 from distal hub 125-1 and then proximally past loop 140-1. The proximal most implant 104-2 can be released by withdrawing enlarged end 150 past proximal loop 140-2 and recess 162.

Additional implants 104 can be included in the chain of sequentially releasably implants by repeating the configuration of loop interlock 404. For example, a third implant (not shown) can be positioned between implants 104-1 and 104-2. The third implant can have a proximal hub and loop like that of implant 104-1, which can be used to interlock with the distal hub and loop of implant 104-2. The third implant can also have a distal hub and loop like that of implant 104-2, which can be used to interlock with the proximal hub and loop of implant 104-1. By adding implants in this fashion, any number of implants can be serially releasably coupled together. It should be noted that all of the loops 140 and 404 can be formed in any manner described herein, including but not limited to the manner described with respect to FIG. 1C. Likewise, this multiple implant embodiment can be used with any of the other embodiments described herein, including implants with multiple bodies as described with respect to FIG. 3, and the passive detachment embodiments described below (e.g., as a coupling between the proximal-most implant and the pusher). This multiple implant embodiment can be used with the variation in control wire routing described with respect to FIG. 1E, for example, the control wire can extend alongside the connected implant hubs passing through only the opposing loops and not the adjacent pair of implant hubs themselves.

Example Embodiments of Systems with Fiber Ball Release Structures

Figure 5A:
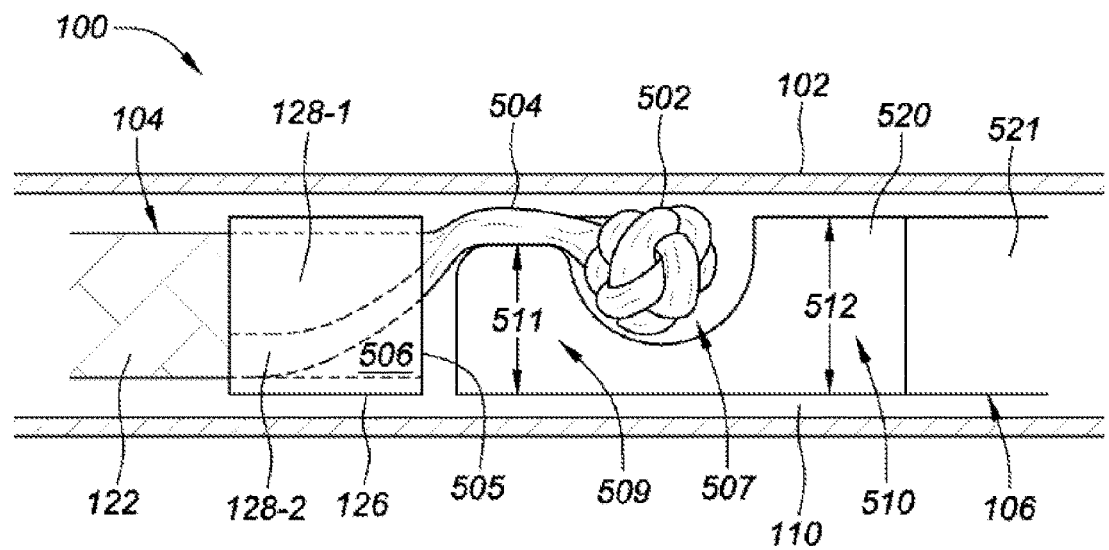
FIGS. 5A-5B are partial cross-sectional views depicting another example embodiment of a delivery system for an occlusive implant with a fiber-based release structure at various stages of deployment.

FIGS. 5A-E depict example embodiments of system 100 adapted for use with a passive proximal detachment structure in the form of a fiber-based ball. FIG. 5A is a partial cross-sectional view depicting an example embodiment of implant 104 releasably coupled with pusher 106. A ball 502 is present on a proximal portion of a fiber or tether extension 504 that extends proximally from a proximal terminus 505 of proximal hub 126 of implant 104. Ball 502 may also be referred to as a globular portion. Ball 502 and extension 504 are formed from fibers. In many embodiments, ball 502 and extension 504 are formed from the fibers that form braid covering 122.

Figure 5B:
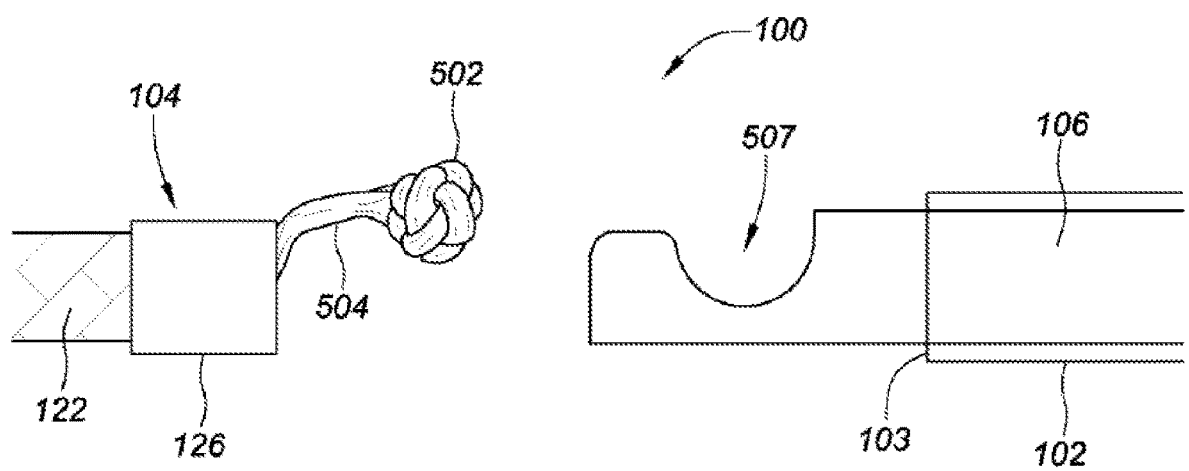

Ball 502 is captured within a recess or opening 507 of pusher 106 and maintained in recess 507 by the constraining sidewalls of catheter 102. The height 511 of a section 509 of pusher 106 distally adjacent to recess 507 is relatively less than the height 512 of a section 510 of pusher 106 located proximal to recess 507. This provides a channel over the radially facing surface of section 509 through which extension 504 can pass. The width of ball 502 is greater than the available space between section 509 and the sidewall of catheter 102, and therefore ball 502 is retained within recess 507. Upon advancement from catheter 102, ball 502 is free to exit recess 507, as depicted in FIG. 5B. At this point, implant 104 is detached from pusher 106 and the remainder of system 100.

As described with respect to fiber loop 140, any one or more fibers from braid 122 can be used to form extension 504 and ball 502. This can include, for example, one braid grouping 128-1 or multiple braid groupings 128-1 and 128-2, etc., including all of the braid groupings constituting braid covering 122. In some embodiments, only a portion of one braid grouping is used to form extension 504 and ball 502. In some embodiments, only a single fiber is used to form extension 504 and ball 502. When less than all fibers are used, the excess fibers can be trimmed away.

Although not limited to such, in many embodiments ball 502 is in the form of a knot. It can be desirable to utilize a knot type that is self-cinching when placed in tension and creates enough mass to secure implant 104 within recess 507. Depending on the type of material and thickness of the fibers used in braid 122, different types of knots may be employed for this purpose. A self-cinching knot minimizes or eliminates the propensity for the knot to slide and effectively increase the length of extension 504, which could lead to increased delivery friction due to the presence of extra fiber material in between pusher 106 and the implant's proximal end.

Figure 5C:
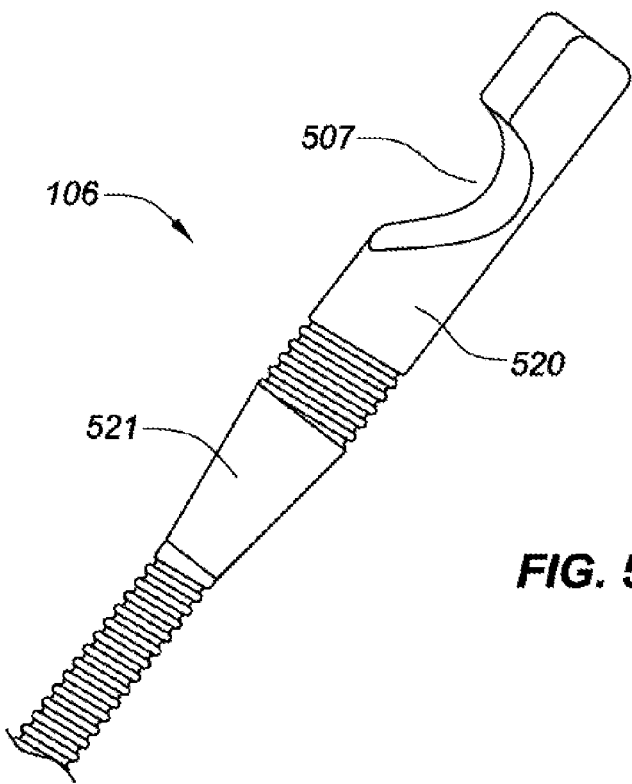
FIG. 5C is a photograph of an example embodiment of a pusher.
Figure 5D:
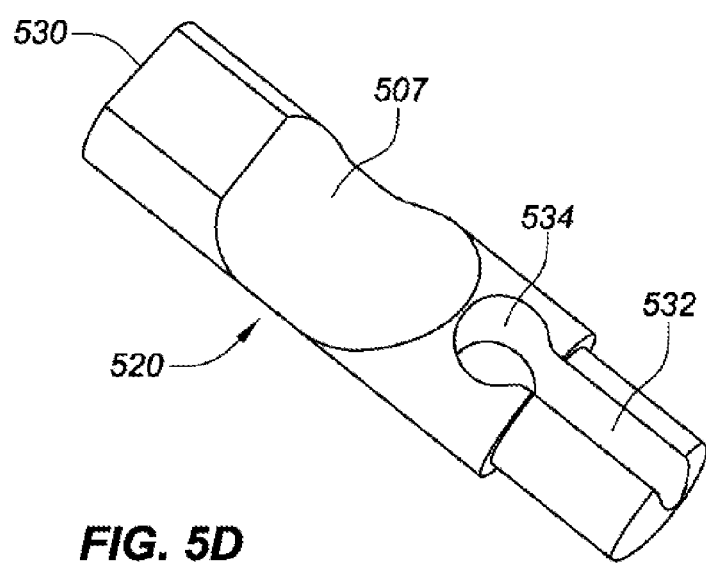
FIG. 5D is a photograph of an example embodiment of a coupler component of a pusher.

FIG. 5C is a photograph depicting pusher 106 with two primary components, a rigid coupler 520 (having recess 507) and a shaft 521. FIG. 5D is a photograph depicting coupler 520 in isolation. Coupler 520 is preferably a rigid component that is secured to the tip of shaft 521 via mechanical connection and/or a bonding material such as solder, adhesive or bonding process such as welding or brazing. Coupler 520 can be made from stainless steel or a radiopaque metal such as platinum or alloy such as platinum/iridium or platinum/tungsten. In some embodiments, coupler 520 can be fabricated from a biocompatible polymer.

The geometry of coupler 520 contains features designed to provide the function of implant advancement and retraction as well as improved release. The front (distally facing) edge 530 (FIG. 5D) of coupler 520 is preferably flat and pushes on what is preferably a rigid proximal end of implant 104 during advancement of implant 104 through catheter 102. The inside edges of recess 507 are preferably angled to allow for relatively effortless release of ball 502 when the junction is advanced past the catheter tip. The presence of squared (i.e., 90° angled) sides increases the need for manipulation of pusher 106 to cause disengagement of implant 104 from pusher 106. The proximal end of coupler 520 may also contain features such as a slot 532 and keyhole or through hole 534 to accommodate a ball-end wire. Such an interface creates a mechanical connection between coupler 520 and the ball-end wire, increasing the tensile strength of this junction.

Figure 5E:
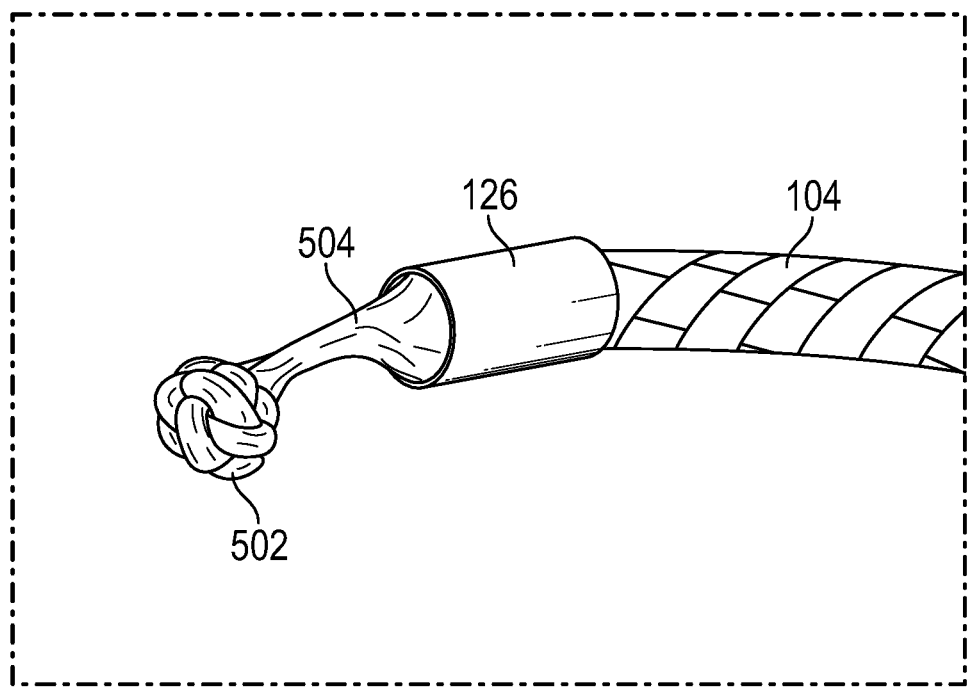
FIG. 5E is a photograph of a proximal end of an example embodiment of an implant having a fiber-based release structure.

FIG. 5E is a photograph of a proximal end of implant 104 having the fiber-based ball 502 and extension 504. The overall length and flexibility of extension 504 allows the junction to traverse small radius vessels with reduced delivery friction versus other interlocking detachment systems that utilize symmetrical, rigid couplers on both the pusher and the implant.

In this photograph, ball 502 is configured as a knot. To further secure knot 502, it may be required to trim the loose ends past the knot and heat those ends so as to melt them in such a fashion as to prevent knot 502 from loosening when placed in tension. This can be accomplished by using a conductive, radiant or convective heat source or some other form of energy source such as a laser. An alternative embodiment to secure the knot from loosening is to apply a small amount of adhesive, such as a UV curable acrylated urethane, or other biocompatible cyanoacrylate, epoxy or silicone adhesive. Adhesive can be used with or without the heat forming of the loose ends past knot 502 and the adhesive also creates a more uniform, spherical termination of the implant.

As stated earlier, the fibers that form the braid covering of implant 104 can be made from a high tensile strength polymer such as UHMWPE and may be braided, twisted or otherwise wrapped around the implant circumference and terminated to form extension 504 and knot 502. Such materials can provide the majority of tensile strength of implant 104 and can also form the mechanical connection to pusher 106, thereby eliminating the need for a mating coupler attached to the end of implant 104. In this manner, the number of components required for passive detachment is reduced by utilizing the fiber already present in the implant.

The fibers are secured at the proximal end of implant 104 preferably underneath proximal hub 126 in the form of a radiopaque marker band. The marker bands described herein can be made from platinum, platinum/iridium, platinum/tungsten, gold, or other radiopaque material and helps to locate the proximal end of the implant under fluoroscopy. A rigid hub 126 also provides a rigid edge on which coupler 520 can contact for advancement of the implant through the delivery catheter. The hub 126 can be secured to the implant's proximal end using a UV curable adhesive and/or by mechanically swaging the marker band on the implant (see also FIG. 5A, depicting inner lumen 506 of hub 126 that can be filled with adhesive).

In some embodiments, it can be desirable to bunch the braid fibers as tightly as possible to one side underneath hub 126 to form as tight a tether extension 504 as possible and to reduce the chance of extension 504 catching or hooking around the front edge of coupler 520.

Figure 6A:
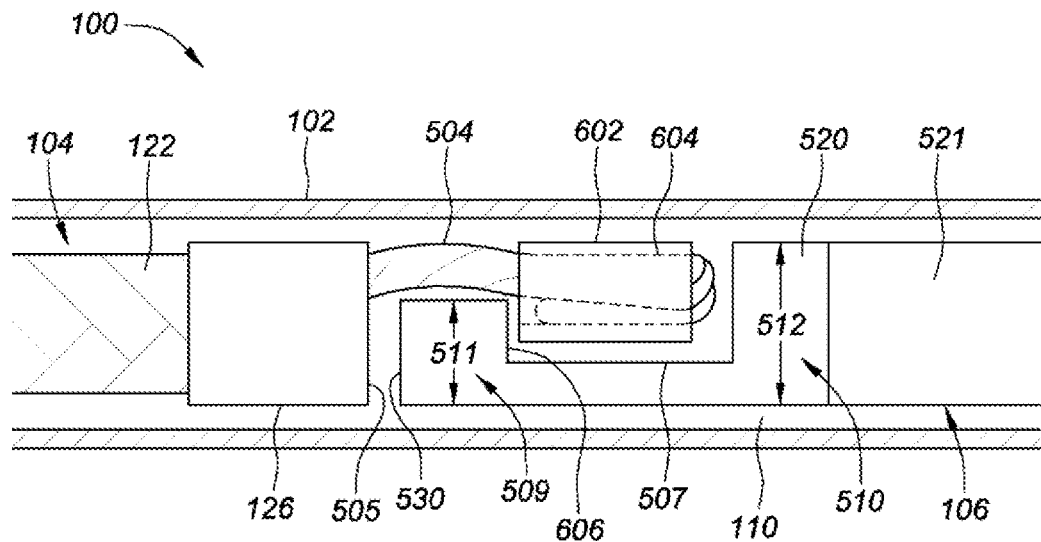
FIGS. 6A-6B are partial cross-sectional views depicting another example embodiment of a delivery system for an occlusive implant with a fiber-based release structure at various stages of deployment.
Figure 6B:
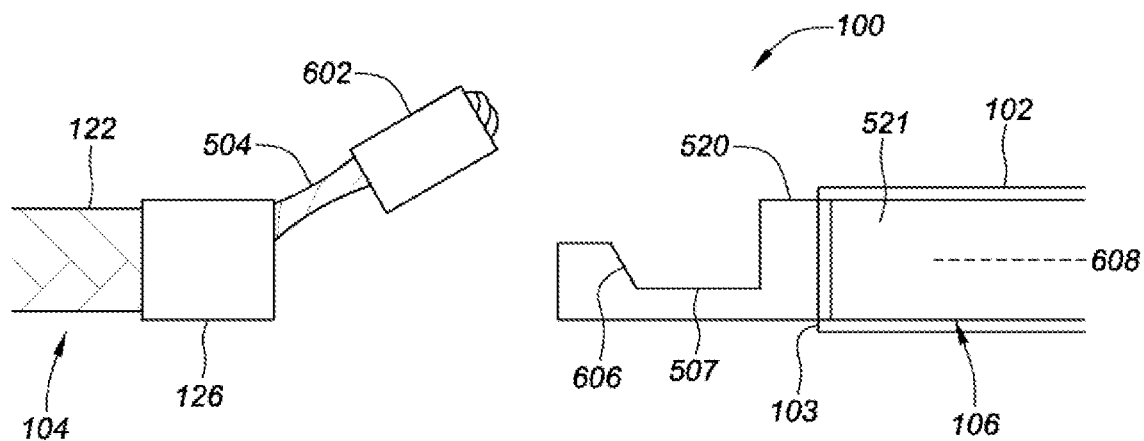

FIGS. 6A-6B are side and top down partial cross-sectional views, respectively, depicting another example embodiment of system 100 with a passive proximal detachment structure similar to that described with respect to FIGS. 5A-5E except that fiber ball 502 is replaced with a tubular section 602. Tether extension 504 extends proximally from proximal terminus 505 of proximal hub 126 of implant 104 and a proximal portion of extension 504 is coupled with tubular section 602. Here, inner lumen 604 of tubular section 602 is shown with dashed lines and extension 504 is shown folded back (e.g., doubled back) within lumen 604. This folded back portion of extension 504 can be secured within lumen 604 by adhesive (e.g., such as those described herein), crimping of tubular section 602, and/or other techniques. In another embodiment, extension 504 can be threaded through lumen 602, wrapped around the outermost surface of tubular section 602, and secured with extension 504 along the length of extension 504 between hub 126 and tubular section 602 (e.g., such as by tying in a knot, or securing with the clamp, or the like). In yet another embodiment, extension 504 can be knotted on the proximal side of section 602 and on the distal side of section 602 such that section 602 is trapped therebetween. Here, recess 507 has a stepped or polygonal profile that corresponds to the overall profile of tubular section 602.

Distal edge 606 of recess 507 is generally perpendicular to the longitudinal axis of catheter 102, but in other alternative embodiments, distal edge 606 of recess 507 can be angled (e.g., 20-70 degrees) so as to facilitate release. FIG. 6B is a partial cross-sectional view depicting a similar example embodiment to that described with respect to FIG. 6A but with distal surface 606 set at a non-normal angle to longitudinal axis 608 of catheter 102. FIG. 6B shows system 100 immediately after release of tubular section 602 from recess 507, which occurs after pusher 106 has been distally advanced with respect to catheter 102 such that recess 507 exits distal opening 103 (or after catheter 102 has been proximally retracted with respect to pusher 106, or a combination thereof).

Tubular section 602 can be formed of an implantable biocompatible material such as a biocompatible polymer (e.g., PEEK, nylon, etc.) or a biocompatible metal (e.g., platinum, stainless steel, gold, nitinol, etc.). Use of a tubular section 602 with a higher rigidity than fibrous not 502 can have the benefit of relatively lower compression, which can provide a more secure connection between implant 104 and pusher 106. The geometry of tubular section 602 is also more easily designed to correspond directly to (or match) the profile of recess 507. Tubular section 602 can have other non-tubular shapes as well, such as spherical, oblong, cubicle, and so forth. In one embodiment section 602 is spherical with a central hole through which tether extension 502 is threaded and knotted.

Figure 6C:
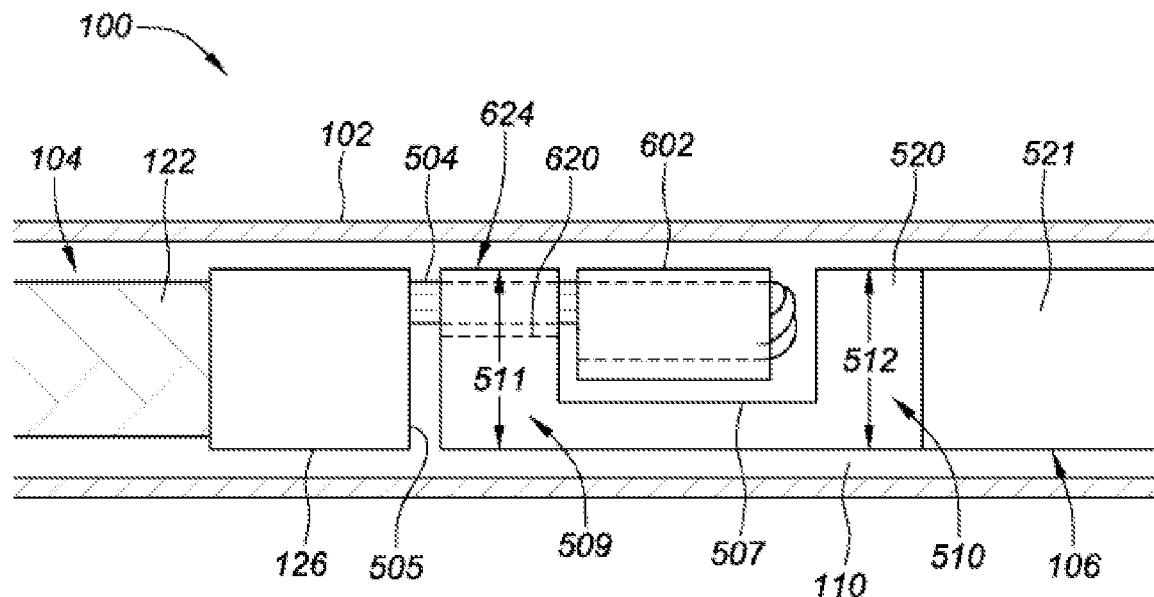
FIGS. 6C-6D are partial cross-sectional views depicting another example embodiment of a delivery system for an occlusive implant with a fiber-based release structure at various stages of deployment.
Figure 6D:
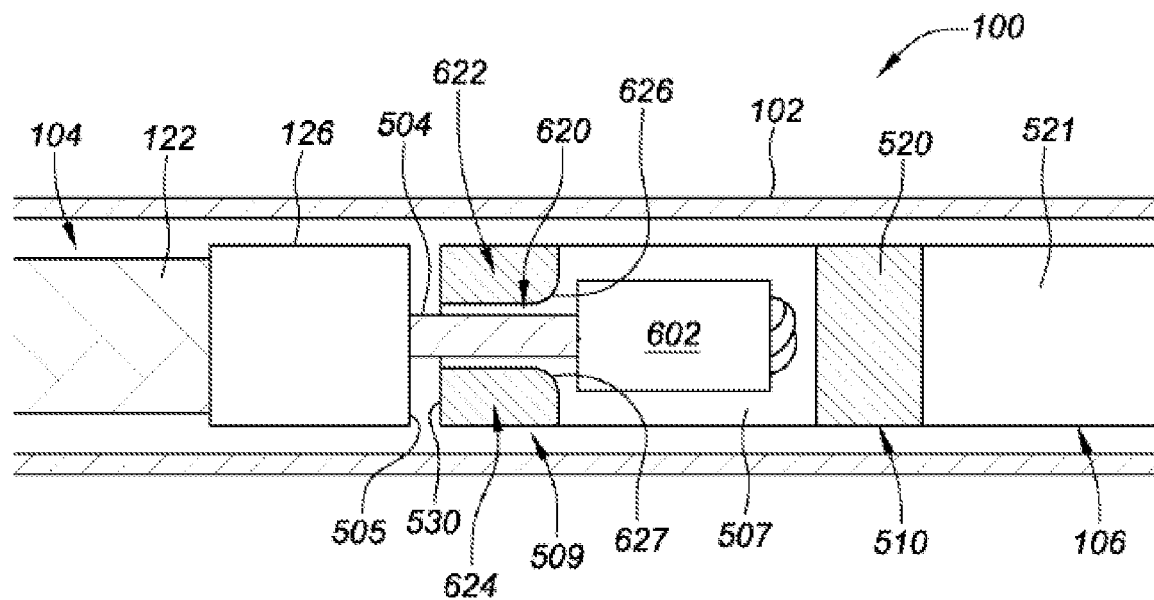

FIGS. 6C-6D are side and top down partial cross-sectional views, respectively, depicting another example embodiment of system 100 having a passive release structure. Here the passive release structure is tubular section 602 but it should be noted that this embodiment can be used with fiber knot 502 or any other passive release structure described herein. This embodiment is similar to that described with respect to FIGS. 6A-6B except height 511 of portion 509 (FIG. 6C) is the same as or similar to height 512 of portion 510, and a channel or slot 620 is present through portion 509 that permits the passage of extension 504 therethrough. The bottom surface of channel 620 is shown with dashed line in FIG. 6C to indicate that it is obscured by raised portion 624, which is shown more clearly in FIG. 6D.

In FIG. 6D, channel 620 can be seen to extend between raised portion 622 and 624, each of which preferably have the same height 511 (FIG. 6C). Interior corners 626 and 627 of raised portions 622 and 624, respectively, can have rounded edges as shown here or a right angle edge. Portions 622 and 624 are generally fillet-shaped from the perspective of FIG. 6D, but portions 622 and 624 can have other profile shapes such as four sided (e.g., square, rectangular, beveled, etc.) or five sided (such as chamfered, etc.) or any other combination of planar and rounded sides. The proximal surfaces of portions 622 and 624 can also be angled like surface 606 of FIG. 6B.

Channel 620 provides a space in which extension 504 can reside and the presence of channel 620 acts to maintain extension 504 in position with respect to coupler 520 and to maintain secure connection between implant 104 and pusher 106. This configuration also reduces contact between tether extension 504 and the interior surface of catheter 102, which can decrease surface friction during delivery and/or retraction. In FIGS. 6A, 6C, and 6D, distal edge 530 of coupler 520 is shown spaced apart from proximal terminus 505 of implant 104, but in practice the surfaces can be designed to be in close proximity or in contact in the positions shown to facilitate the immediate transfer of pushing force from pusher 106 to implant 104. This configuration having channel 620 can also be utilized with the embodiments of FIGS. 5A-5E.

Additional Example Embodiments of Systems with Interlocking Release Structures

Also described herein are example embodiments of system 100 with passive release structures having relatively rigid (or substantially rigid) interlocking configurations as compared to fibers. These embodiments can be utilized to releasably couple implant 104 to pusher 106, or to releasably couple a proximal end of a first implant 104 to a distal end of a second implant 104 (such as in a linear chain). For ease of illustration the example embodiments will be described in the context of releasably coupling implant 104 with pusher 106.

Figure 7A:
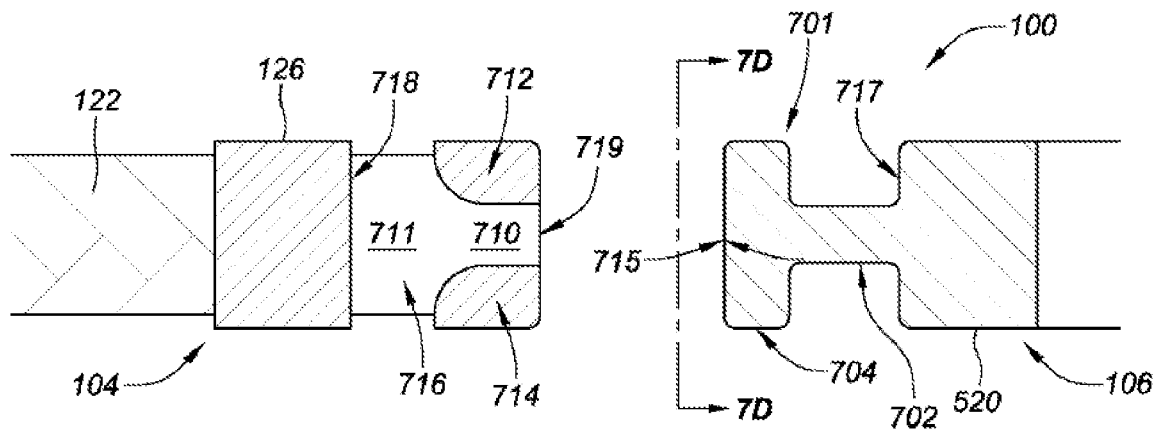
FIG. 7A is a top down view depicting another example embodiment of a delivery system having a passive release structure in an uncoupled state.

FIGS. 7A-7D depict an example embodiment of system 100 where pusher 106 includes a T-shaped portion 701 (FIG. 7A) extending from the base of coupler 520. FIG. 7A is a top-down view depicting pusher 106 and implant 104 in an un-coupled state, such as after release. A longitudinal strut 702 extends from the base of coupler 520 and transitions to a perpendicular lateral strut 704. Proximal hub 126 of implant 104 includes a recess 716 with a profile corresponding to the profile of T-shaped portion 701. Recess 716 includes a longitudinal channel or slot 710, partially bound by raised portions 712 and 714, that corresponds to the profile of longitudinal strut 702 and a connecting lateral channel or slot 711 that corresponds to the profile of lateral strut 704.

Figure 7B:
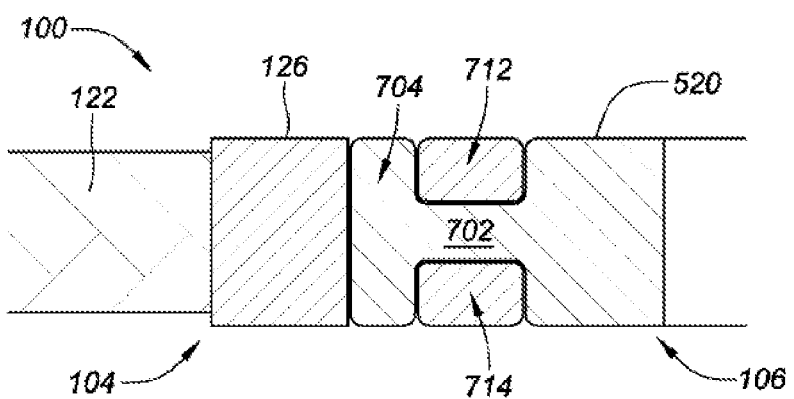
FIGS. 7B and 7C are top down and side views, respectively, of the embodiment of FIG. 7A in a coupled state.
Figure 7C:
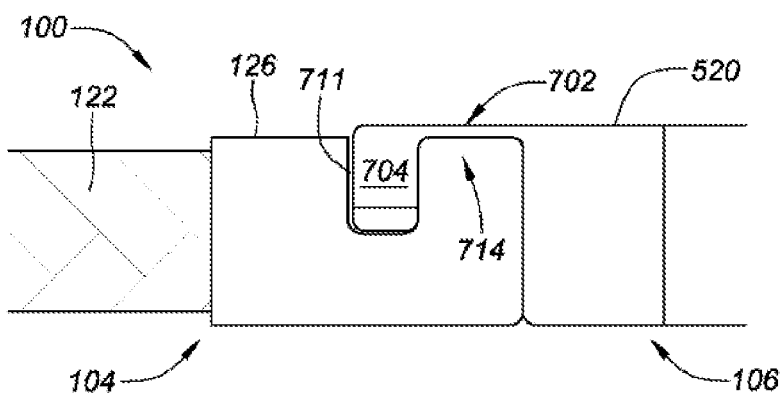

FIGS. 7B and 7C are top down and side views, respectively, depicting this example embodiment of system 100 in a coupled state. Catheter 102 is not shown. Release of implant 104 from pusher 106 can be accomplished in the same manner described earlier, e.g. by exposing coupler 520 and hub 126 from within catheter 102 such that removal of the sidewall of catheter 102 as a restraint permits T-shaped portion 701 to uncouple from (or slip off of) recess 716. Surfaces 715 and 717 of coupler 520 can push on surfaces 718 and 719, respectively, of hub 126 to advance implant 104 within the catheter lumen and/or during the release procedure.

Figure 7D:
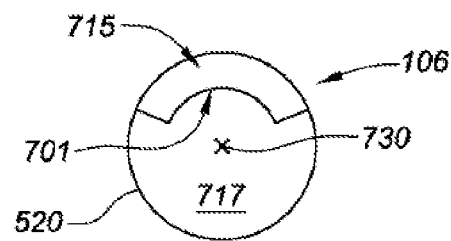
FIG. 7D is an end on view taken along line 7D-7D of FIG. 7A.

FIG. 7D is an end on view of pusher 106 taken along line 7D-7D of FIG. 7A, and depicts the overall cylindrical profile of coupler 520 with T-shaped portion 701. In some embodiments, a section of a cylindrical rod can be used to create coupler 520 by removing the undesired material to fashion the T-shaped portion 701, such as by grinding, etching, and so forth. In other embodiments, coupler 520 can be formed from a section of a hypotube or other tubular member and T-shaped portion 701 can be formed from the sidewall of the tube. As seen in FIG. 7D, T-shaped portion 701 curves about a longitudinal central axis 730 of pusher 106.

A potential advantage of the embodiment of FIGS. 7A-7D is that coupler 520 and hub 126 may be fabricated with a relatively shorter longitudinal length than other embodiments described herein, increasing the ability for the junction to traverse small radius vessels. The configuration can be reversed such that the male T-shaped portion 701 extends proximally from a base of hub 126 and the corresponding recess 716 is present in coupler 520. The extension of T-shaped portion 701 proximally from implant 104 can facilitate retrieval of implant 104 after release, such as with a tether or snare.

Figure 8A:
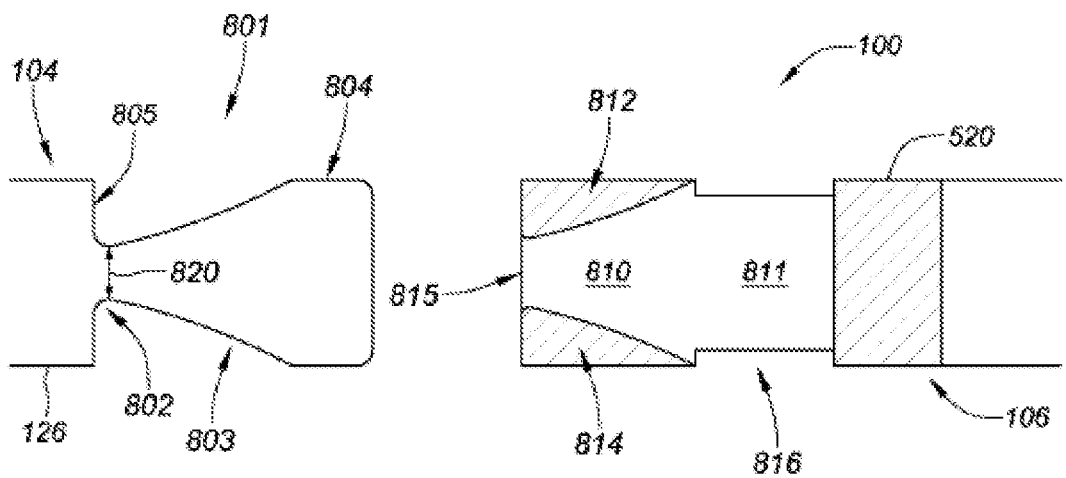
FIG. 8A is a top down view depicting another example embodiment of a delivery system having a passive release structure in an uncoupled state.
Figure 8B:
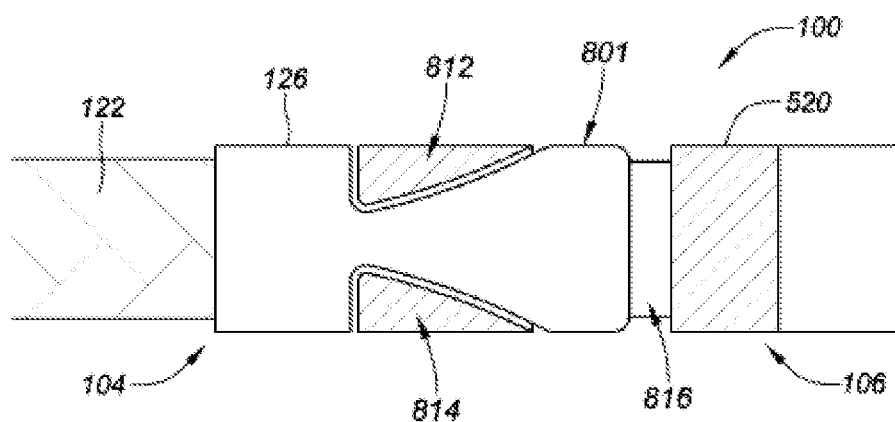
FIGS. 8B and 8C are top down and side views, respectively, of the embodiment of FIG. 8A in a coupled state.
Figure 8C:
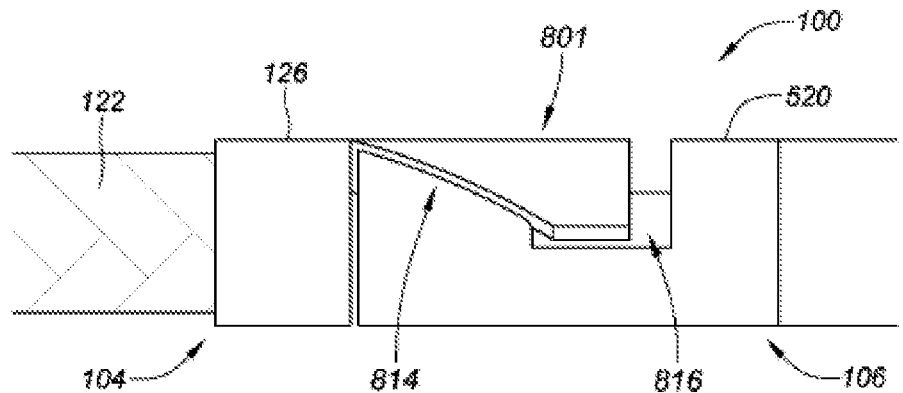

FIGS. 8A-8C depict another example embodiment of system 100 having a passive release structure. Here, a V-shaped portion 801 extends proximally from a base 805 of hub 126 of implant 104 and is configured to mate with a corresponding geometry of recess 816 in coupler 520. FIG. 8A is a top down view depicting system 100 in an uncoupled state and FIGS. 8B and 8C are top down and side views, respectively, depicting system 100 in a coupled state (catheter 102 is not shown). As can be seen in FIG. 8A, V-shaped portion 801 generally widens as it extends proximally from the base 805 of hub 126. V-shaped portion 801 has a base 802 where width 820 is at a relative minimum, and width 820 increases in neck region 803, either at an increasing rate (as shown here) or at a constant or decreasing rate, and then width 820 maintains a constant value in head region 804. Put differently, portion 801 tapers or flares laterally outward as it extends proximally from the base 805 of hub 126. Although not shown directly, V-shaped portion 801 can have an end on profile similar to that depicted in FIG. 7D.

FIGS. 8A-8C depict another example embodiment of system 100 having a passive release structure. Here, a V-shaped portion 801 extends proximally from a base 805 of hub 126 of implant 104 and is configured to mate with a corresponding geometry of recess 816 in coupler 520. FIG. 8A is a top down view depicting system 100 in an uncoupled state and FIGS. 8B and 8C are top down and side views, respectively, depicting system 100 in a coupled state (catheter 102 is not shown). As can be seen in FIG. 8A, V-shaped portion 801 generally widens as it extends proximally from the base 805 of hub 126. V-shaped portion 801 has a base 802 where width 820 is at a relative minimum, and width 820 increases in neck region 803, either at an increasing rate (as shown here) or at a constant or decreasing rate, and then width 820 maintains a constant value in head region 804. Put differently, portion 801 tapers or flares laterally outward as it extends proximally from the base 805 of hub 126. Although not shown directly, V-shaped portion 801 can have an end on profile similar to that depicted in FIG. 7D.

Recess 816 of coupler 520 as to raised portions 812 and 814 with a profile that is generally the reverse of neck region 803 so as to create a channel 810 in which neck region 803 fits. Head portion 804 is configured to be placed in channel 811 located proximal to portions 812 and 814, wherein surface 815 may abut or nearly abut hub 126. Release of V-shaped portion 801 can be accomplished in the same or similar manners to that of the other embodiments described herein. The use of a V-shape, in some embodiments, may facilitate release as compared to other configurations such as the T-shape of FIGS. 7A-7D. The configuration can be reversed such that the male V-shaped portion 801 extends distally from a base of coupler 502 and the corresponding recess 816 is present in hub 126. The embodiments described with respect to FIGS. 7A-8C can have other shapes as well and are not limited to T and V shapes and corresponding recesses.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A medical system, comprising:
an occlusive implant having a distal end and a proximal end, the occlusive implant comprising a flexible body with a covering that comprises a plurality of fibers in the form of a braid, wherein at least one fiber of the plurality of fibers extends from the covering in the form of a loop at the proximal end of the occlusive implant;
an elongate tubular member having an inner lumen; and
an elongate pusher member slidable within the inner lumen and having a distal end region with a recess adapted to releasably hold the at least one fiber in the form of the loop.

2. The medical system of claim 1, wherein the occlusive implant comprises a proximal hub, the at least one fiber in the form of the loop extending proximally from the proximal hub.

3. The medical system of claim 2, wherein the pusher member is a tubular member with a sidewall and an inner lumen, the recess being an opening in the sidewall providing access to the inner lumen of the pusher member, wherein the medical system further comprises an elongate control wire positionable within the inner lumen of the pusher member both distally and proximally of the recess such that the at least one fiber in the form of the loop is releasably secured within the recess by the control wire.

4. The medical system of claim 2, wherein the pusher member is a tubular member with a sidewall and an inner lumen, the recess being an opening in the sidewall providing access to the inner lumen of the pusher member, wherein the medical system further comprises an elongate control wire.

5. The medical system of claim 4, wherein the elongate control wire extends distally within the inner lumen of the pusher member from a proximal location of the pusher member and exits the pusher member through the recess.

6. The medical system of claim 5, wherein the loop extends into an open end of the pusher member and around the elongate control wire.

7. The medical system of claim 6, wherein the elongate control wire extends distally alongside the occlusive implant and is releasably secured to the distal end of the occlusive implant.

8. The medical system of claim 1, wherein the loop is a first loop and wherein at least one fiber of the plurality of fibers extends from the covering in the form of a second loop at the distal end of the occlusive implant.

9. The medical system of claim 8, wherein the occlusive implant is a first occlusive implant, the medical system comprising a second occlusive implant having a second distal end and a second proximal end, the second occlusive implant comprising a second flexible body with a second covering that comprises a second plurality of fibers in the form of a braid, wherein at least one fiber of the second plurality of fibers extends from the second covering in the form of a third loop at the second proximal end of the second occlusive implant.

10. The medical system of claim 1, wherein the body of the occlusive implant is adapted to transition from an elongate shape to a secondary shape in the form of a coil.

11. A method of delivering an occlusive implant, comprising:
positioning an open distal end of an elongate tubular member in proximity to a target delivery site, wherein a pusher member is releasably secured to an occlusive implant within an inner lumen of the elongate tubular member;
advancing the pusher member distally to push the occlusive implant from within the inner lumen, the occlusive implant having a distal end and a proximal end, the occlusive implant comprising a flexible body with a covering that comprises a plurality of fibers in the form of a braid, wherein at least one fiber of the plurality of fibers extends from the covering in the form of a loop at the proximal end of the occlusive implant; and
withdrawing an elongate control wire proximally such that the occlusive implant is released from the pusher member after a distal terminus of the elongate control wire is withdrawn through the loop.

12. The method of claim 11, wherein the occlusive implant is a first occlusive implant, and upon positioning an open distal end of an elongate tubular member in proximity to a target delivery site, the first occlusive implant is releasably secured to a second occlusive implant located distal to the first occlusive implant within the inner lumen of the elongate tubular member.

13. The method of claim 12, wherein the loop is a first loop and wherein at least one fiber of the plurality of fibers extends from the covering in the form of a second loop at the distal end of the first occlusive implant.

* * * * *